United States Patent
Rowe et al.

(10) Patent No.: US 9,886,617 B2
(45) Date of Patent: Feb. 6, 2018

(54) MINIATURIZED OPTICAL BIOMETRIC SENSING

(71) Applicant: LUMIDIGM, INC., Albuquerque, NM (US)

(72) Inventors: Robert K. Rowe, Corrales, NM (US); Ryan Eric Martin, Tijeras, NM (US)

(73) Assignee: HID Global Corporation, Austin, TX (US)

( * ) Notice: Subject to any disclaimer, the term of this patent is extended or adjusted under 35 U.S.C. 154(b) by 0 days.

(21) Appl. No.: 14/719,133

(22) Filed: May 21, 2015

(65) Prior Publication Data

US 2015/0254495 A1 Sep. 10, 2015

Related U.S. Application Data

(63) Continuation of application No. PCT/US2014/060271, filed on Oct. 13, 2014.
(Continued)

(51) Int. Cl.
*G06K 9/00* (2006.01)
*A61B 5/1172* (2016.01)
*A61B 5/00* (2006.01)

(52) U.S. Cl.
CPC ........ *G06K 9/00033* (2013.01); *A61B 5/0059* (2013.01); *A61B 5/1172* (2013.01);
(Continued)

(58) Field of Classification Search
None
See application file for complete search history.

(56) References Cited

U.S. PATENT DOCUMENTS

| | | | | |
|---|---|---|---|---|
| 6,081,612 | A * | 6/2000 | Gutkowicz-Krusin | ......... A61B 5/0071 382/128 |
| 6,898,299 | B1 * | 5/2005 | Brooks | ............ G06K 9/00 340/5.52 |

(Continued)

FOREIGN PATENT DOCUMENTS

WO 2008100329 8/2008

OTHER PUBLICATIONS

Rowe, R., Nixon, K., & Butler, P. (2008). Multispectral fingerprint image acquisition. Advances in biometrics, 3-23.*
(Continued)

*Primary Examiner* — Vu Le
*Assistant Examiner* — Samah Beg
(74) *Attorney, Agent, or Firm* — Marsh Fischmann & Breyfogle LLP; Daniel J. Sherwinter

(57) ABSTRACT

Systems and methods are described for providing reliable biometric access control using an optical biometric sensor in a miniaturized form factor. Some implementations include multiple light sources that can illuminate skin or other tissue at multiple locations during a single measurement session. An imaging array can be arranged to form images of the light exiting the tissue only after undergoing diffuse reflectance in the tissue. Some implementations use the images to perform biometric functions. For example, the images can be used to identify an individual, verify identity of an individual, estimate demographic characteristics of an individual, etc. Such biometric functions can further be used to determine and affect access to secured assets.

20 Claims, 18 Drawing Sheets
(7 of 18 Drawing Sheet(s) Filed in Color)

Related U.S. Application Data

(60) Provisional application No. 61/890,091, filed on Oct. 11, 2013, provisional application No. 61/947,293, filed on Mar. 3, 2014.

(52) U.S. Cl.
CPC ........ G06K 9/00046 (2013.01); *A61B 5/6891* (2013.01); *A61B 5/6898* (2013.01); *G06K 2009/0006* (2013.01)

(56) References Cited

U.S. PATENT DOCUMENTS

| | | | | |
|---|---|---|---|---|
| 7,995,808 B2* | 8/2011 | Rowe | ................ | G06K 9/00033 382/124 |
| 8,285,010 B2* | 10/2012 | Rowe | ................ | A61B 5/0059 382/115 |
| 8,675,925 B2* | 3/2014 | Derakhshani | ...... | G06K 9/00597 382/115 |
| 8,965,064 B2* | 2/2015 | Hanna | ................ | G06K 9/00604 351/206 |
| 2002/0183624 A1 | 12/2002 | Rowe | | |
| 2004/0120553 A1* | 6/2004 | Stobbe | ................ | A61B 5/0064 382/115 |
| 2004/0240712 A1* | 12/2004 | Rowe | ..................... | A61B 5/117 382/124 |
| 2005/0063573 A1 | 3/2005 | Setlak | | |
| 2005/0185847 A1* | 8/2005 | Rowe | ................ | G06K 9/0004 382/224 |
| 2005/0205667 A1* | 9/2005 | Rowe | ................ | A61B 5/0059 235/382 |
| 2006/0110015 A1 | 5/2006 | Rowe | | |
| 2006/0244947 A1* | 11/2006 | Rowe | ................ | G06K 9/00046 356/71 |
| 2006/0274921 A1* | 12/2006 | Rowe | ................ | G06K 9/00033 382/124 |
| 2007/0030475 A1* | 2/2007 | Rowe | ..................... | A61B 5/117 356/71 |
| 2008/0013805 A1* | 1/2008 | Sengupta | ............... | G06K 9/001 382/124 |
| 2011/0199183 A1* | 8/2011 | Marsden | ............ | G07C 9/00563 340/5.52 |
| 2012/0025951 A1* | 2/2012 | Rowe | ................ | G06K 9/00046 340/5.83 |
| 2012/0062364 A1 | 3/2012 | Rowe | | |
| 2012/0229816 A1* | 9/2012 | Rodrigue | ............. | G01B 11/245 356/610 |
| 2013/0272585 A1* | 10/2013 | Mueller | ............... | G06K 9/0004 382/124 |
| 2015/0244950 A1* | 8/2015 | Johnson | ................ | H04N 5/3535 348/296 |
| 2015/0337571 A1* | 11/2015 | Henderson | ............. | E05B 85/16 701/49 |

OTHER PUBLICATIONS

International Serach Report and Written Opinion for Application No. PCT/US2014/060271 mailed Jan. 20, 2015, 13 pages.

* cited by examiner

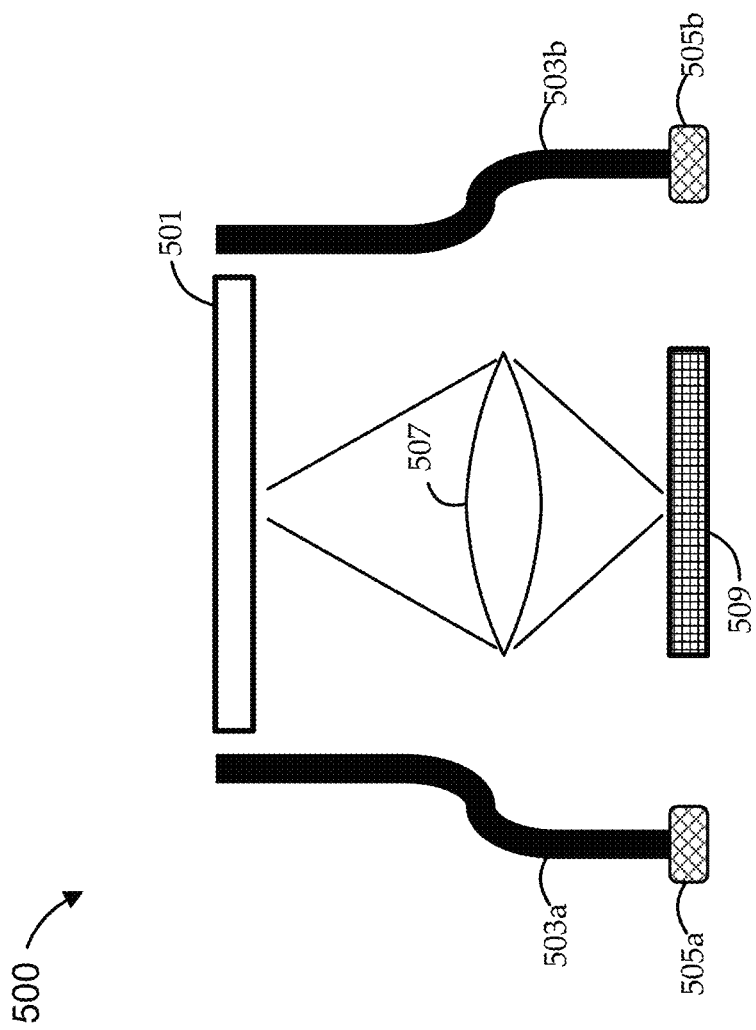

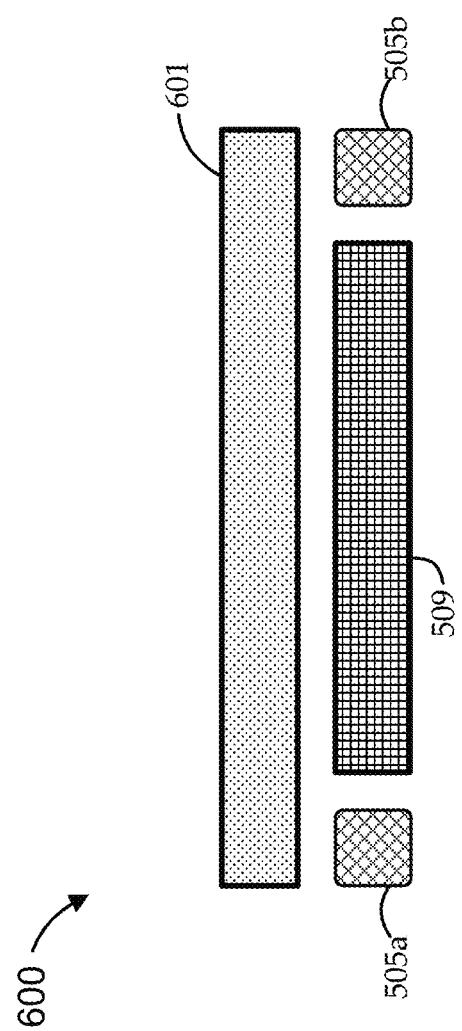

US 9,886,617 B2

MINIATURIZED OPTICAL BIOMETRIC SENSING

FIELD

Embodiments relate generally to biometrics, and, more particularly, to miniaturized optical biometric sensing systems and techniques.

BACKGROUND

There are many scenarios in which individuals desire to limit or otherwise control access to assets. For example, individuals may desire to control access to data stored on a smart phone or other portable electronic device, to locations secured by door locks or other mechanisms, to industrial equipment for use only by authorized personnel, to firearms or controlled substances, etc. A number of physical and logical access controls are available for such scenarios, including keys, passwords, credentials, etc. Increasingly, individuals and organizations are seeking biometric solutions for access control. However, traditional biometric detection systems can be too large, expensive, unreliable, and/or otherwise undesirable to implement in many contexts.

In particular, traditional optical biometric approaches tend to be too large to implement in a miniaturized form factor and/or too expensive to implement in commodity-type consumer goods (e.g., integrated into a smart phone, a door lock, an industrial equipment button, etc.). Further, traditional approaches (especially smaller and less expensive approaches) tend to have limited reliability across wide operating conditions, such as with high variability in finger skin wetness or dryness, ambient lighting conditions, etc.; and/or limited ability to distinguish between a genuine skin site and a spoof (any of a variety of means and materials presented to the sensor in an attempt to replicate a genuine finger and thereby defeat the security of the system).

BRIEF SUMMARY

Among other things, systems and methods are described herein for providing reliable biometric access control using an optical biometric sensor in a miniaturized form factor. Some implementations include multiple light sources that can illuminate skin or other tissue at multiple locations during a single measurement session. An imaging array can be arranged to form images of the light exiting the tissue after undergoing diffuse reflectance in the tissue. For example, rather than imaging light reflected and/or scattered from the surface of the tissue, or directly from the light sources without interacting with the tissue at all, the imaging array can be implemented to only receive light that has passed into and interacted with subsurface portions of the tissue. Some implementations use the images to perform biometric functions. For example, the images can be used to identify an individual, verify identity of an individual, estimate demographic characteristics of an individual, etc. Such biometric functions can further be used to determine and affect access to secured assets (e.g., rooms, computational systems, stored digital information, physical storage cabinets, controlled substances, etc.).

According to one set of embodiments, a biometric access system is provided. The system includes a biometric sensor system that has: an interface subsystem with an interface surface disposed to contact purported tissue of a subject; an illumination subsystem disposed to pass source illumination into the purported tissue of a subject via a set of first surface regions of the purported tissue; and a detector subsystem disposed to acquire a number of images corresponding to a number of optical imaging conditions, the number of images being based on response illumination exiting a set of second surface regions of the purported tissue, the set of second surface regions being different from the set of first surface regions, the response illumination produced by interactions between the source illumination and subsurface characteristics of the purported tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

The present disclosure is described in conjunction with the appended figures:

FIG. 5 shows an illustrative biometric sensor, according to various embodiments;

FIG. 6 shows another illustrative biometric sensor, according to various embodiments;

In the appended figures, similar components and/or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION

In the following description, numerous specific details are set forth to provide a thorough understanding of various embodiments. However, one having ordinary skill in the art should recognize that the invention can be practiced without these specific details. In some instances, circuits, structures, and techniques have not been shown in detail to avoid obscuring embodiments.

In a number of scenarios, it can be desirable to limit or otherwise control access to assets using a miniaturized biometric sensor. For example, traditional biometric approaches, particularly optical sensor-based approaches, tend to be too large to implement in a miniaturized form factor and/or too expensive to implement in commodity-type consumer goods (e.g., integrated into a smart phone, a door lock, an industrial equipment button, etc.). Further, traditional approaches (especially smaller and less expensive approaches) tend to have limited reliability across wide operating conditions, such as with high variability in finger skin wetness or dryness, ambient lighting conditions, etc.; and/or limited ability to distinguish between a genuine skin site and a spoof (any of a variety of means and materials presented to the sensor in an attempt to replicate a genuine finger and thereby defeat the security of the system).

Some embodiments described herein provide reliable biometric access control using an optical biometric sensor in a miniaturized form factor. Some implementations include multiple light sources that can illuminate skin or other tissue at multiple locations during a single measurement session. An imaging array can be arranged to form images of the light exiting the tissue after undergoing diffuse reflectance in the tissue. For example, rather than imaging light reflected and/or scattered from the surface of the tissue, or directly from the light sources without interacting with the tissue at all, the imaging array can be implemented to only receive light that has passed into and interacted with subsurface portions of the tissue. Some implementations use the images to perform biometric functions. For example, the images can be used to identify an individual, verify identity of an individual, estimate demographic characteristics of an individual, etc. Such biometric functions can further be used to determine and affect access to secured assets (e.g., rooms, computational systems, stored digital information, physical storage cabinets, controlled substances, etc.).

Figure 1:
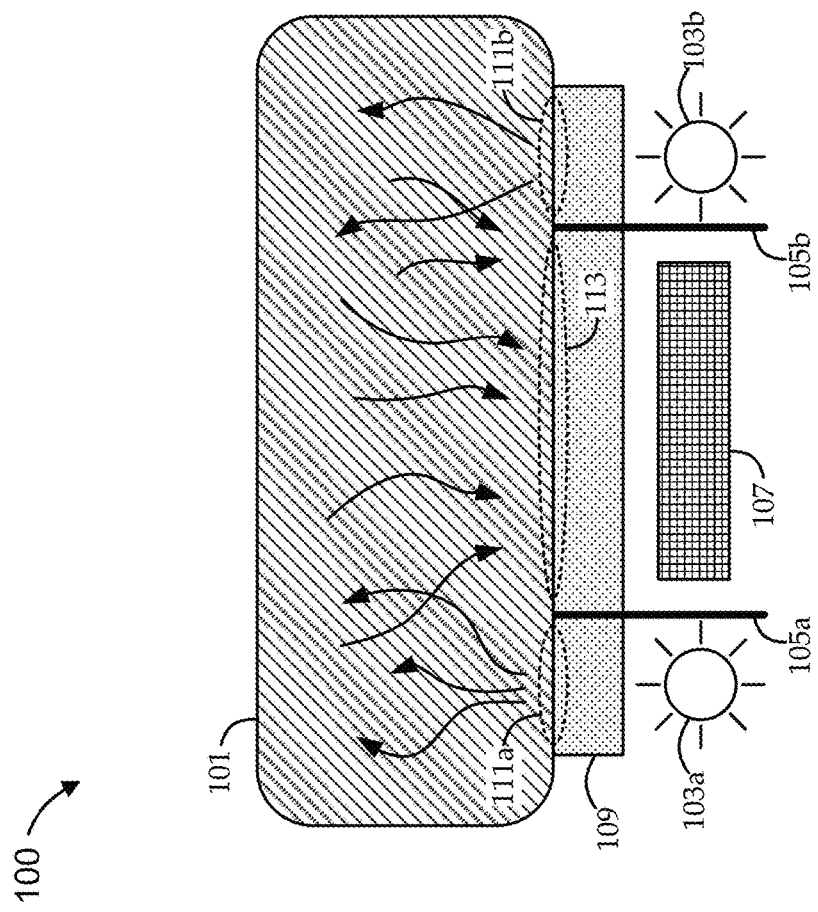
FIG. 1 shows an illustrative biometric sensor, according to various embodiments.

FIG. 1 shows an illustrative biometric sensor 100, according to various embodiments. The biometric sensor 100 includes an interface subsystem 109, an illumination subsystem 103, and a detector subsystem 107. For context, purported tissue 101 of a subject (e.g., a finger, a spoof intended to fraudulently represent a finger, etc.) is shown in contact with an interface surface of the interface subsystem 109. While the purported tissue 101 is shown in contact with the interface surface, some implementations can operate when the purported tissue 101 is in partial contact with the interface surface, or in close proximity to the interface surface. Further, various embodiments are implemented as a miniaturized biometric sensor 100, so that the interface surface is sized to accommodate only a small portion of a fingerprint.

The purported tissue 101 (skin, or other tissue being imaged, etc.) can be human skin. In some instances, the skin site being imaged can be located on the palmar side of the hand and can include portions of the palm or fingers and thumbs. In some embodiments, the skin site can be located on the palmer surface of the distal joint of the fingers or thumbs. The terms "finger," "fingerprint," and the like are used herein to refer broadly to the skin site (or purported skin site) being imaged, even thought the tissue site may or may not contain skin and further may or may not encompass portions of fingerprints of the fingers or thumbs.

Embodiments of the illumination subsystem 103 include a set (i.e., one or more) of illumination sources. For example, multiple illumination sources can be arranged to pass source illumination into the purported tissue 101 via a set of first surface regions 111 of the purported tissue 101. In one embodiment, the light sources can be light emitting diodes (LEDs) and may further be LEDs that have different wavelength characteristics.

Embodiments of the detector subsystem 107 can include an imager, such as an imaging array. In one embodiment, the imaging array can be a silicon imaging array and may further be a CMOS or CCD imaging array. In some embodiments, the imaging array can include a color filter array such as a Bayer pattern. In other embodiments, the imaging array can omit the color filter array, and the array elements can each be sensitive to a broad distribution of wavelengths of light. Other implementations can include any suitable optics, such as color filters, polarization filters, lenses, mirrors, etc. Embodiments of the detector subsystem 107 are disposed to acquire at least one image (e.g., a single image, an image stack, etc.) corresponding to a plurality of optical imaging conditions. The at least one image can be based on response illumination exiting a set of second surface regions 113 of the purported tissue 101.

Various embodiments of the illumination subsystem 103 and detector subsystem 107 can include (e.g., or be in optical communication with interface subsystem 109 elements that include) optical elements for relaying illumination to and/or from the purported tissue 101. For example, illumination can be relayed from the illumination subsystem 103 into the purported tissue 101 and/or from the purported tissue 101 to the detector subsystem 107 using one or more lenses, lenslet arrays, mirrors, fiber-optics, gradient-index (GRIN) lenses, SELFOC-type microlenses, and/or any suitable combination of optical elements. Further, in some implementations, illumination elements of the illumination subsystem 103 and imaging elements of the detector subsystem 107 may not be co-planar, such that different approaches can be used to relay the illumination to and/or from the purported tissue 101. For example, in one implementation, fiber-optic wave guides can be used to couple the source illumination from multiple illumination sources of the illumination subsystem 103 into the purported tissue 101, and a lenslet array can be used to direct the diffusely reflected response illumination from the purported tissue 101 to an imaging array of the detector subsystem 107.

Figure 2:
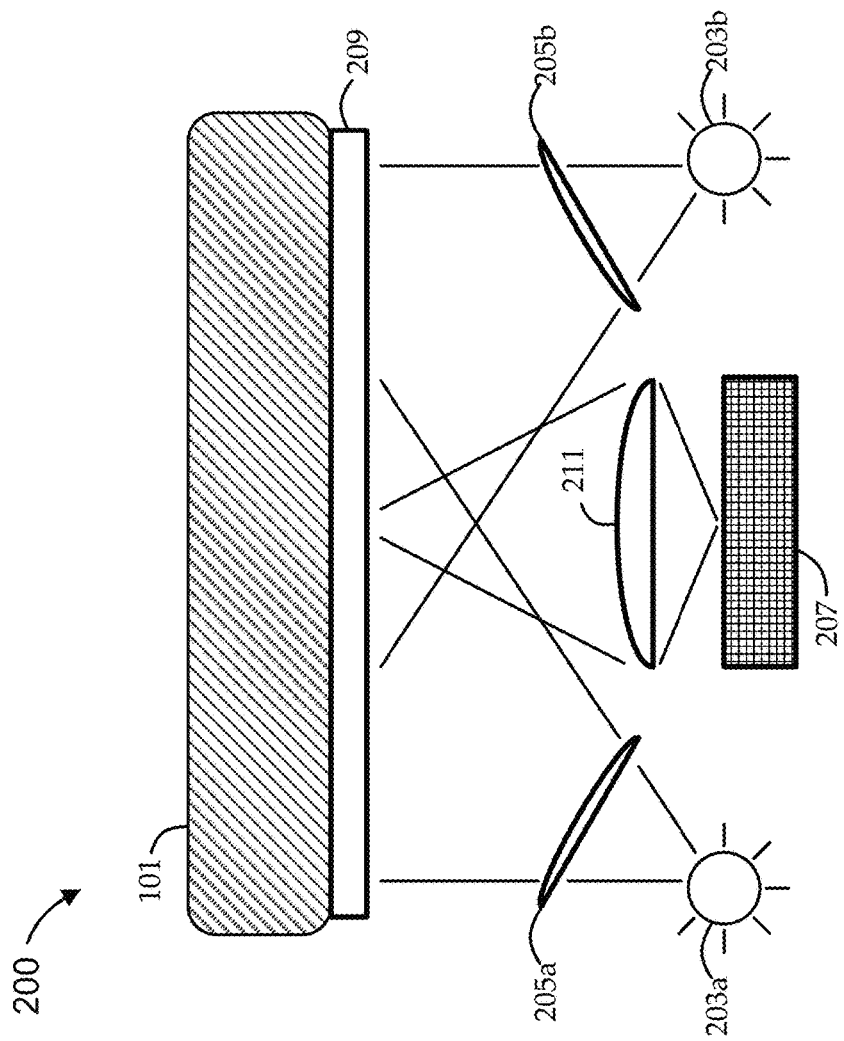
FIG. 2 shows an illustrative traditional biometric sensor for the sake of added context.

FIG. 2 shows an illustrative traditional biometric sensor 200 for the sake of added context. As shown, the traditional biometric sensor 200 can include illumination sources 203, a detector 207, and a platen 209. Purported tissue 101 in contact with the platen 209 can be illuminated by the illumination sources 203 via the platen 209, and light reflected and/or scattered by the surface of the purported tissue 101 can be imaged by the detector 207. In such a traditional biometric sensor 200, a broad area of the purported tissue 101 is illuminated by the illumination sources 203 through the platen 209 (e.g., using illumination optics 205). The broadly illuminated area can then be imaged by detector 207 using imaging optics 211 through the platen 209. There is generally no requirement that the light from the illumination sources 203 propagates through subsurface portions of the purported tissue 101. In fact, many such traditional biometric sensors 200 rely on total internal reflectance (TIR) and/or other optical effects at the interface between the surface of the purported tissue 101 and the platen (e.g., the difference in index of refraction between a platen-air interface and a platen-tissue interface).

Returning to FIG. 1, in contrast to the traditional implementation shown in FIG. 2, embodiments are implementated so that the first surface regions 111 are optically separate from the second surface regions 113 of the purported tissue 101. In effect, the purported tissue 101 can essentially become the source of illumination from the perspective of the detector subsystem 107. For example, as illustrated, optical blockers 105 can be used to substantially block the source illumination from reaching the detector subsystem 107 without first passing through the purported tissue 101. Such optical isolation can be accomplished in a variety of ways and does not necessarily require separate optical components for this purpose. For example, the source illumination transmitted from the illumination subsystem 103 to the purported tissue 101 and/or from the purported tissue 101 to the detector subsystem 107 can be collimated, focused, coherent, or otherwise arranged, such that multiple interactions and/or optical scattering events will generally occur within the purported tissue 101 before the source illumination can reach the detector subsystem 107. Additionally or alternatively, the paths to and from the purported tissue 101 can be isolated by the use of shields, masks, light pipes, filters, opaque coatings, etc. In one embodiment, illumination sources can be highly directional and positioned either in contact with fiber-optic light guides, a fiber-optic face plate, in direct contact with the purported tissue 101, etc. Such configurations reduce or substantially eliminate the amount of light that can pass from the illumination subsystem 103 to the detector subsystem 107 without being diffusely reflected by the purported tissue 101.

In general, the source illumination enters the purported tissue 101 and undergoes diffuse reflectance below the surface of the skin. During such subsurface interactions, the illumination is affected by scattering, absorption, changes in refractive index, and other such optical characteristics of the purported tissue 101. After the illumination undergoes diffuse reflection below the surface of the purported tissue 101, a portion of the illumination exits the purported tissue 101 in the direction of the illumination subsystem 103. The exiting ("response") illumination is effectively a portion of the source illumination that entered the purported tissue 101 and underwent subsurface optical interactions (e.g., diffuse reflectance). The exiting response illumination can pass through the illumination subsystem 103 and be used to form the at least one image by the detector subsystem 107.

In some implementations, the interface subsystem 109 includes a fiber-optic faceplate. For example, a portion of the response illumination exits the purported tissue 101 within an acceptance angle of the fiber-optic faceplate. Such light can pass through the faceplate and strike an imaging array of the detector subsystem 107, from which the detector subsystem 107 can form an image (e.g., an array of values corresponding to sensor position of a two-dimensional array when the sensor position is spatially correlated to portions of the skin being imaged).

Various embodiments include multiple illumination sources that are arranged around the periphery of an imaging region of the interface subsystem 109 (e.g., substantially corresponding to second surface regions 113). Alternatively or additionally, the illumination from some or all of those sources is guided to enter the purported tissue 101 at locations around the periphery of the imaging region of the interface subsystem 109. As described above, a fiber-optic faceplate can be used to optically relay the features of the region of purported tissue 101 being imaged to an imaging array. In another embodiment, one or more lenses, lenslet arrays, mirrors, gradient-index (GRIN) lenses, SELFOC-type microlenses, and/or any suitable combination of optical elements can be used to optically relay the features of the region of purported tissue 101 being imaged to the imaging array or other components of the detector subsystem 107.

Different types of illumination (e.g., different wavelengths, intensities, etc.) have certain propagation characteristics through tissue. For example, some illumination wavelengths experience a generally small amount of optical scattering in skin tissue and/or the scattering is non-isotropic. Accordingly, the number and positions of illumination sources, wavelengths and/or intensities of illumination sources, illumination angles and/or other geometries, additional optics (e.g., filters, lenses, etc.), exposure times, maximum size of an imager of the detector subsystem 107 (e.g., an imaging array), and/or other features of the biometric sensor 100 can be selected to be consistent with such optical propagation characteristics of live, human finger tissue, or the like. For example, the biometric sensor 100 can be designed to have an optical distance between the illumination sources and the imager that corresponds to an average path traversed by the illumination through the purported tissue 101 as it travels from an entry point to an exit point through the purported tissue 101.

In some embodiments, a single image or set of images (e.g. taken at multiple exposure values) is acquired when each of the illumination sources is illuminated. For example, an image stack can be generated, and each image of the image stack can correspond to a particular illumination condition. In certain implementations, images are acquired for different exposure times at each illumination condition. For example, each of a number of illumination conditions are activated at three exposure times (e.g., 5, 10, and 20 milliseconds), and at least one corresponding image is acquired for each illumination condition at each exposure time. In some embodiments, multiple illumination sources may be illuminated during the acquisition of a single image. In general, the multiple images acquired from multiple illumination conditions can be affected by differing influences of scatter, absorbance, refractive indices, and other optical characteristics in the purported tissue 101 being imaged, as well as geometric differences between the area of illumination and components of the detector subsystem 107 (e.g., imaging array), etc.

The images can be processed separately or combined together in some way. In one embodiment, each of the images corresponding to the illumination sources with substantially the same wavelength characteristics are combined together. In one embodiment, the multiple illumination sources include red, green, and blue LEDs, and the resulting images are combined together to form a color image having red, green and blue components. In another embodiment, all of the images corresponding to different illumination conditions are combined together to form a single monochromatic image.

In some embodiments, the multiple images are processed to perform a biometric function. In some embodiments, the biometric function includes identification of a person or verification of the identity of a person. In some embodiments, the biometric function can be the estimation of demographic characteristics of the person touching the sensor. Such characteristics can include an estimate of the person's age, gender, ethnicity, profession, etc.

In some embodiments, the biometric function can include spoof detection, such as confirming that the sample being presented to the sensor includes genuine tissue (e.g., of the type expected from a living, human finger); rather than an attempt to use an altered finger, artificial material, or other means to defeat the security of the sensor (e.g., non-human tissue, non-living human tissue, etc.). The spoof detection can be performed in a number of ways. In some implementations, machine learning is used to develop model criteria for distinguishing genuine, live tissue from a spoof. Some embodiments use a color contrast and/or color fall-off model for spoof detection. For example, implementations can illuminate the finger with multiple colors, and genuine tissue can manifest a characteristic drop-off of each color over distance (e.g., a spatial frequency of a high-frequency structure), which would not be present in some or all categories of spoofs. Some implementations use multiple spoof detection techniques in conjunction. For example, some spoof detection techniques are used to detect certain categories of spoofs, thereby narrowing the number of spoofs to which machine learning and/or other techniques are applied.

In some embodiments, the multiple images can be processed to filter and emphasize certain spatial frequencies or other image characteristics. In some embodiments, image characteristics corresponding to low spatial frequencies may be used alone or in combination with other instrumental characteristics to perform spoof detection as well as identity verification and/or identification and other such tasks. In some embodiments, the higher spatial frequencies of the plurality of images can be combined together to form a representation of the dermatoglyphic patterns of the skin. In some embodiments, such fingerprint image(s) can be analyzed to perform identity verification, and/or identification, as well as to perform spoof detection and other such tasks.

In some embodiments, the multiple images acquired from a finger are analyzed to determine a degree of touch. For example, analysis of the image stack can indicate whether the user is touching the sensor lightly or is pressing heavily on the sensor.

Figure 3:
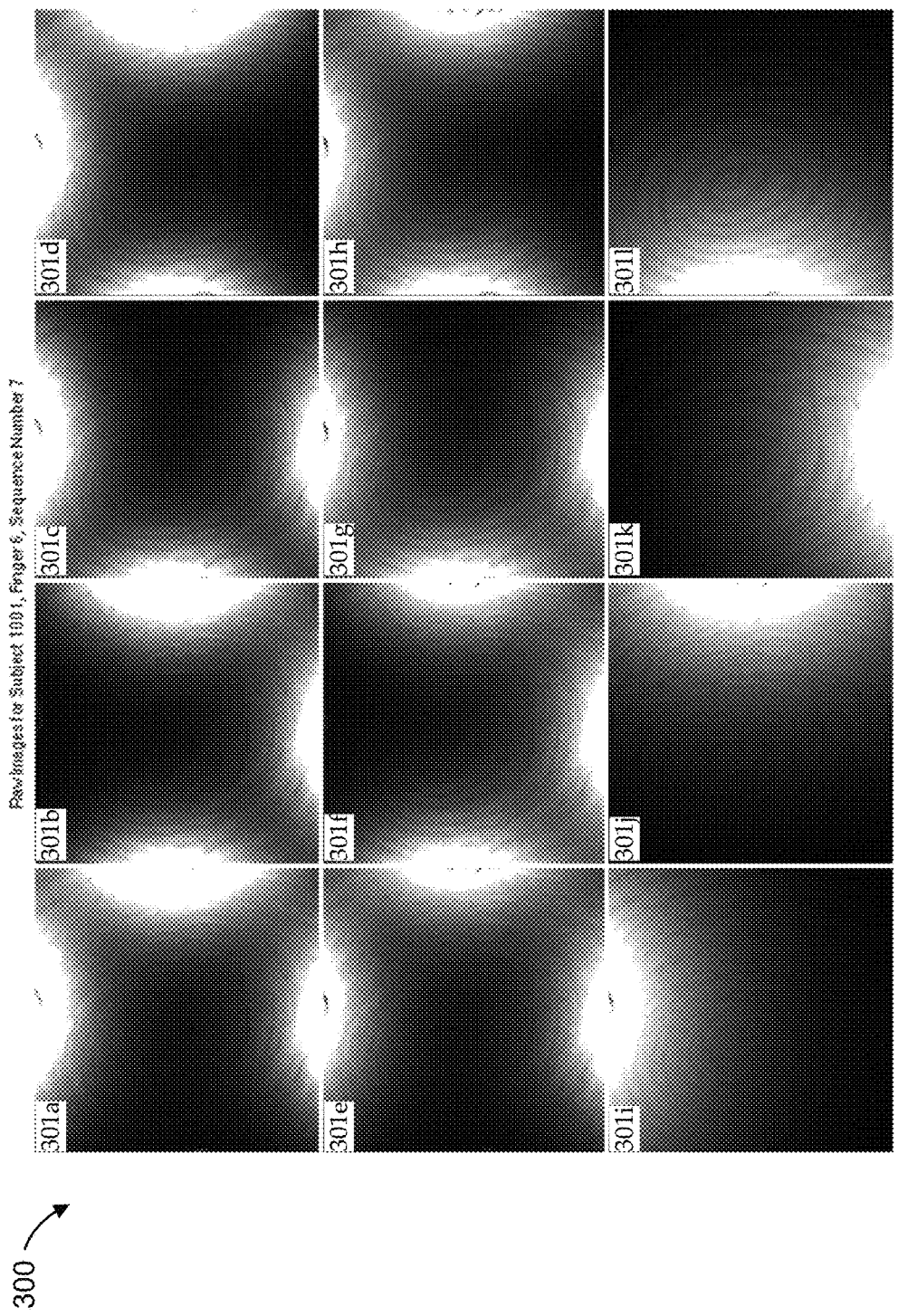
FIG. 3 shows a sequence of twelve illustrative images of a finger taken under different optical imaging conditions.
Figure 4:
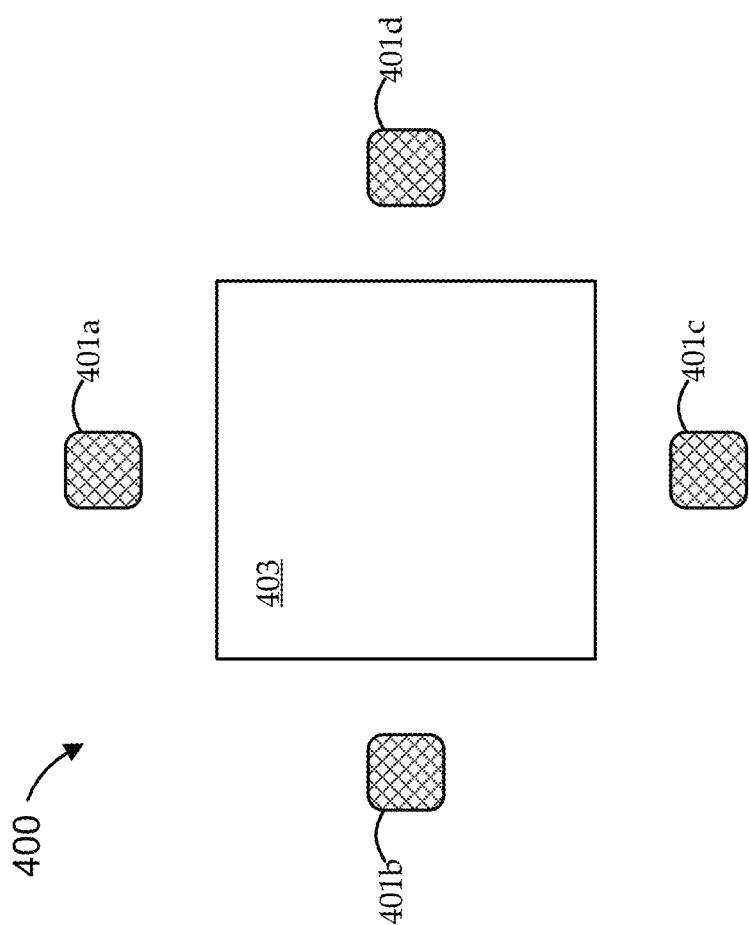
FIG. 4 shows a simplified diagram of an illustrative arrangement used to collect the images of FIG. 3.

FIG. 3 shows a sequence of twelve illustrative images of a finger taken under different optical imaging conditions (e.g., different illumination conditions). FIG. 4 shows a simplified diagram of an illustrative arrangement used to collect the images 301 of FIG. 3. Four LED packages 401 are arranged to illuminate the periphery of an imaging area 403 (e.g., an imaging region of an interface subsystem). Each of the LED packages 401 includes an RGB (red-green-blue) triplet of LED die that can be separately controlled to emit variable amounts of red, green, and/or blue light from each of the packages 401. To acquire the images shown in FIG. 3, all the LED packages 401 can be controlled to emit a single color. For example, images 301a, 301b, 301c, 301d are illustratively acquired using LEDs emitting blue light; images 301e, 301f, 301g, 301h are illustratively acquired using LEDs emitting green light; and images 301i, 301j, 301k, 301l are illustratively acquired using LEDs emitting red light.

As can be seen from the images 301, the intensity of the light passing through and being diffusely reflected by subsurface skin falls off relatively rapidly as the distance from the light source to the point of skin being imaged increases. Moreover, the light from the blue and green LEDs generally propagates less far through skin than does the light from the red LED. For this reason, some implementations acquire images 301 corresponding to blue or green illumination using concurrent illumination from multiple blue or green LED packages 401, while images 301 corresponding to blue or green illumination can be acquired using fewer (e.g., a single) LED packages 401. For example, image 301a was acquired with the blue LEDs of packages 401a, 401d, and 401c illuminated; image 301g was acquired with green LEDs of packages 401a, 401d, and 401c illuminated; and image 301i was acquired with the red LED of package 401a illuminated. Other configurations and combinations of LEDs illuminated per raw image can be used with these and/or other implementations.

For the sake of illustration, the object-space pixel resolution of the images 301 of FIG. 3 is approximately 1500 pixels per inch (ppi). Such a relatively high resolution may be beneficial to acquire and use very fine details of a fingerprint, including pores, ridge shape, incipient ridges, and other such details (e.g., known in the art as "Level III" information). Such high resolution may also be useful for acquiring biometric information from babies, young children and others who have very fine or delicate fingerprint structures. Many current standard fingerprint sensors are designed with a spatial resolution of approximately 500 ppi, and some fingerprint sensors considered as high-resolution commonly support 1000 ppi imaging. Various embodiments of the biometric sensor 100 described herein can be implemented with a wide range of image resolutions from below 100 ppi to more than 2000 ppi, which can be beneficially used in a variety of applications.

The size of the region of skin being imaged in the images 301 is approximately 0.22-by-0.22 inches. As described above, due to the relatively short propagation of blue and green light in skin, each of the blue and green images can be illuminated with fewer illumination sources that those used for the red images. The relatively larger propagation of red light through human skin is due in part to the lower absorbance of blood at red wavelengths relative to those at blue or green. Other implementations can use alternative and, or additional wavelengths (e.g., including visible combinations of light, infrared illumination, wide-band sources of illumination, etc.). For example, infrared illumination light can enable imaging of a larger area of skin than with visible wavelengths, as the propagation of infrared light at certain wavelengths can be longer than that of red light. Near infrared wavelengths up to the cutoff of silicon detectors (~1300 nm) can be advantageously employed to illuminate skin. In addition to the ability to use some near infrared wavelengths to illuminate larger areas of skin than feasible with equivalent visible light sources, non visible illumination may be desirable for certain applications. In other embodiments, infrared illumination and visible illumination, and even very near ultraviolet illumination may be combined together advantageously for various biometric tasks such as spoof detection and the estimation of various demographic parameters as well as for identification and verification.

The images 301 shows in FIG. 3 were acquired using a monochromatic silicon imager 403. Alternatively, the imager 403 can be implemented as a color imager of various kinds. For example, the color imager can use a color filter array having color filter elements that cover each image pixel in such a way that each pixel "sees" only selected wavelengths. One such arrangement of color filters is known as a Bayer pattern comprised of red, green and blue color filter elements, though other variants can be used. In cases where the imager 403 is a color imager, multiple illumination wavelengths can be illuminated during each image acquisition (e.g., during each acquisition session, frame, etc.). For example, one or more blue LEDs can be turned on simultaneously with one or more red LEDs and the two illumination conditions can be separated by extracting the blue and red pixels of the image array, or may be interpolated to form an RGB representation. In other embodiments, broad-spectrum illumination such as white-light LEDs can be used for illumination with a color imager (such broad spectrum illuminators can also be used with a monochromatic imager, for example, with the spectral content integrated by the imager rather than separated as in the case of a color imager). In some cases infrared illumination can be used advantageously in conjunction with visible illuminators and a color imager, for example, because many such color filter arrays tend to pass infrared light with little or no discrimination among some or all of the visible-light filter elements. As such, a color imager can act to distinguish between colors in the visible region but can also have properties of a monochromatic array when illuminated with appropriate infrared light.

As used herein, phrases, such as multiple "optical conditions," "illumination conditions," "optical imaging conditions," or the like, can generally refer to differences in illumination wavelengths (e.g., single wavelengths, combinations of wavelengths, etc.), illumination geometries (e.g., positions, angles, etc.), illumination patterns, illumination levels (e.g., intensities, exposure times, etc.), acquisition characteristics (e.g., active filter configurations, etc.), and/or any other suitable optical environmental differences between a plurality of acquired images. Furthermore, such plurality of images may be acquired in a plurality of image frames or using a single image frame. A single image frame can be used (e.g. in the case of an imager with a color filter array that can be simultaneously collect light from two or more illumination sources in different positions and different colors). Such multiple illumination conditions can be then separated from the single image by various means. For example, if the different light sources are substantially monochromatic with wavelengths that correspond to different color filters of a Bayer color filter array then the individual single-color subarrays may be extracted from the resulting image. Alternatively, the raw color image may be interpolated to produce a standard RGB color image. The color planes of such image may then be analyzed separately or combined together in a variety of ways in accordance with the present invention.

FIG. 5 shows an illustrative biometric sensor 500, according to various embodiments. The biometric sensor 500 can be an alternative implementation of the biometric sensor 100 shown in FIG. 1 and/or an illustrative implementations of the arrangement 400 shown in FIG. 4, and such a biometric sensor 500 can be used, for example, to acquire the images 300 shown in FIG. 3. As illustrated, the biometric sensor 500 includes an interface subsystem (e.g., a platen 501), an illumination subsystem (e.g., having a number of illumination sources 505 and optical guides 503), and a detector subsystem (e.g., having an imager 509 and imaging optics 507). The illumination sources 505 can be LEDs, laser diodes, quantum dots, incandescent sources, and/or any other suitable illumination source. The optical guides 503 (e.g., optical fibers, waveguides, light pipes, diffusers, polarizers, optical filters, and/or any other suitable optical guides, or the like) can optically couple source illumination from the illumination sources 505 to the edges of an imaging area (e.g., corresponding to the platen 501). The source illumination can enter purported tissue (not shown) via the optical guides 503, the entering illumination can undergo subsurface diffuse reflectance in the purported tissue, and some of the illumination can exit through the platen 501 as response illumination. The response illumination can be directed via the platen 501 and imaging optics 507 (e.g., a lens, multiple lenses, a lenslet array, plane mirrors, focusing mirrors, polarizers, GRIN lenses, and/or any other suitable imaging optics 507) to the imager 509 (e.g., an imaging array).

FIG. 6 shows another illustrative biometric sensor 600, according to various embodiments. The biometric sensor 600 can be an alternative implementation of the biometric sensor 100 of FIG. 1, the biometric sensor 500 of FIG. 5, etc. As illustrated, the biometric sensor 600 includes an interface subsystem (e.g., a fiber-optic faceplate 601), an illumination subsystem (e.g., having a number of illumination sources 505), and a detector subsystem (e.g., having an imager 509). Source illumination from the illumination sources 505 can enter purported tissue (not shown) through one or more first (e.g., peripheral) regions of the fiber-optic faceplate 601, the entering illumination can undergo subsurface diffuse reflectance in the purported tissue, and some of the illumination can exit the purported tissue at one or more second (e.g., central) regions of the fiber-optic faceplate 601 as response illumination. The response illumination can be directed via the fiber-optic faceplate 601 to the imager 509. Alternatively, the illumination sources 505 can illuminate the purported tissue directly (e.g., they can be configured to contact the purported tissue directly or through a thin protective layer, etc.), or via waveguides, light pipes, etc. The fiber-optic faceplate 601 can be replaced by a lenslet array, lenses, mirrors, and/or other suitable optical interface.

Figure 7A:
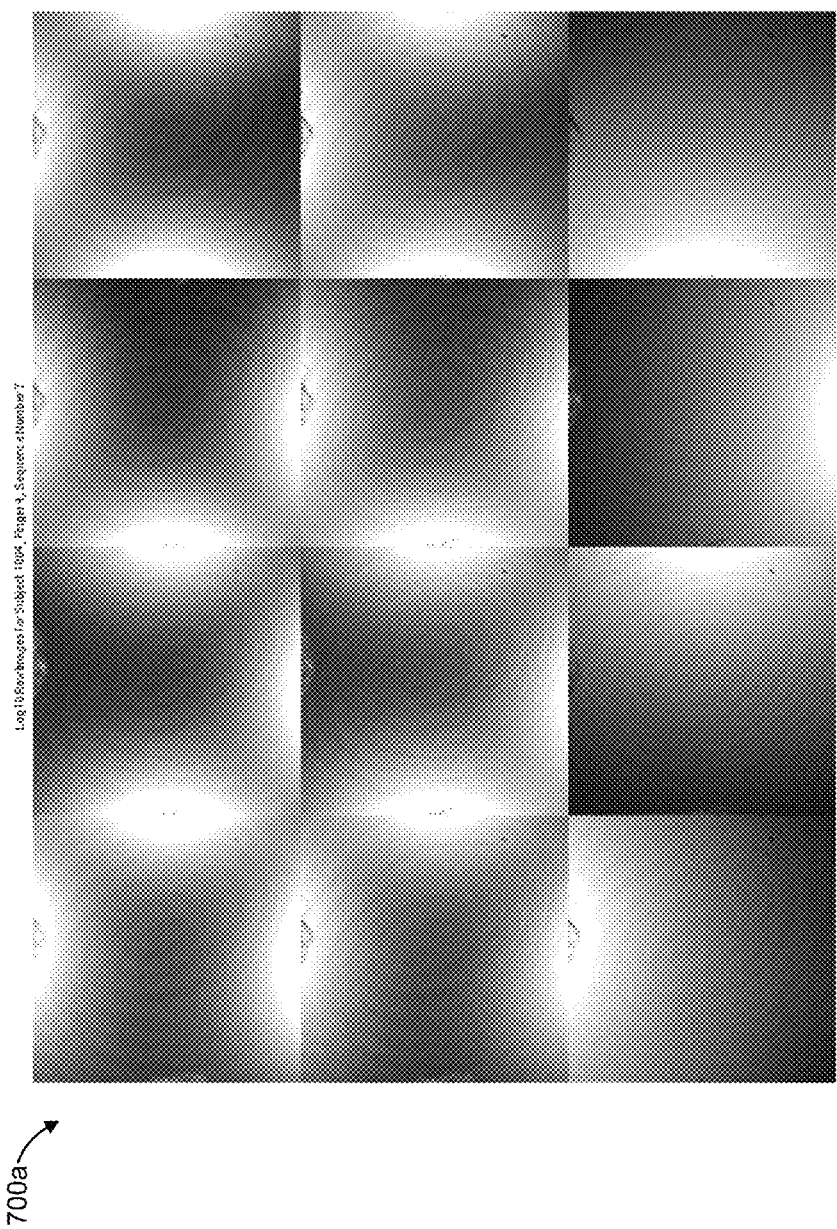
FIG. 7A shows a set of raw images of a finger collected with an 8-bit linear image array.
Figure 7B:
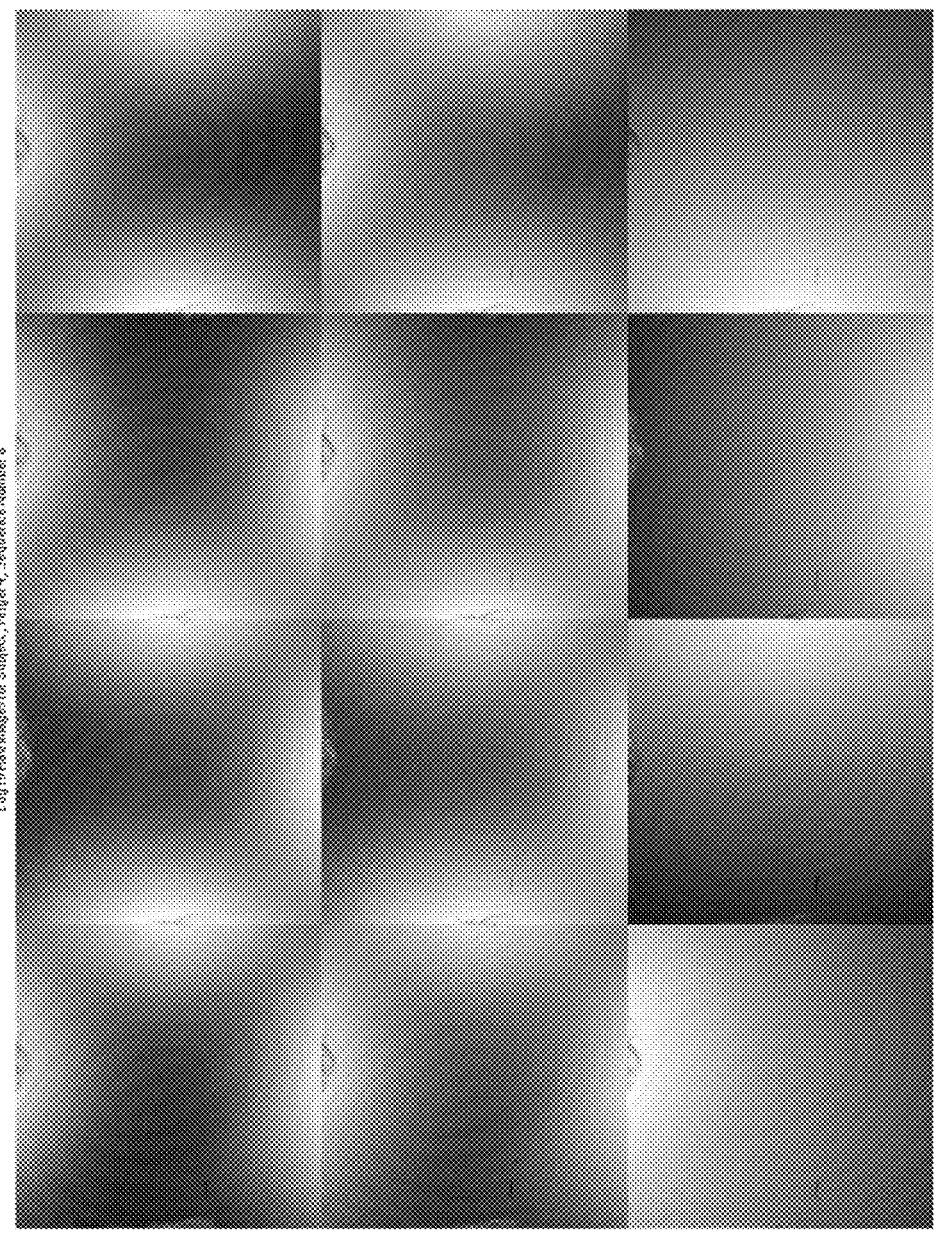
FIG. 7B shows a set of raw images collected with an HDR imager that reports 14-bit images.

In various embodiments, the imager used to collect raw images can have a linear response with respect to light intensity, or can have a non-linear response of some type. For example, an imager capable of high-dynamic range (HDR) imaging can be used to enable light to be collected over a longer image distance, while maintaining gray levels that are neither saturated nor at the noise floor of the imaging system. FIG. 7A shows a set of raw images 700a of a finger collected with an 8-bit linear image array. FIG. 7B shows a set of raw images 700b collected with an HDR imager that reports 14-bit images. Both figures are displayed as log 10 transformations of the actual bit levels to facilitate visual examination. As can be seen, the HDR images 700b have smaller regions of saturation and smaller regions of dark pixel values, as compared to the corresponding linear images 700a.

Raw images similar to those shown in FIG. 3, FIG. 7A, and FIG. 7B can be analyzed in a variety of ways to perform biometric tasks. In one embodiment, the raw images can be mathematically decomposed to quantify the spectral and textural characteristics, and these characteristics can be used alone or in conjunction with other information in order to perform identity verification or identification; spoof detection; estimation of demographic characteristics of age, gender, ethnicity, and other such parameters; etc. Some implementations can perform such characterization using a mathematical decomposition, such as principal component factor analysis, to generate factors for each image plane taken over a representative set of finger images. Other implementations can use Fourier analysis for decomposition, which can be used to find the amount of energy in the raw images that are contained in certain spatial frequency bands and/or angular frequency bands. Other implementations can use wavelet decomposition for such purposes, including, but not limited to, the use of dual-tree complex wavelets. Alternatively, Gabor filters, Laplacian filters, and/or other suitable decomposition techniques can be employed to decompose and quantify elements of the raw images.

Once the raw images are decomposed and quantified, the resulting decomposition coefficients can be used in a variety of classification methods to perform such biometric tasks as spoof detection, gender estimation, ethnicity estimation, identity verification, identification, and/or other classifications. In some cases, the decomposition coefficients can be augmented by other values, such as instrumental and environmental parameters, that can include exposure and gain settings of the imager, drive currents and pulse durations of the LEDs (or comparable characteristics of other types of illumination sources), temperatures of the environment or some portion of the sensor itself, humidity measurements, ambient light measurements, various parameters that may be measured during manufacture of the sensor (e.g., flat field, DC offset, color correction, etc.), etc.

In another embodiment, the raw images can be analyzed to estimate the pressure being used by the user to press the sensor. Changes in the physiology of a user's finger during touch can be manifested in the raw images. These changes can then be quantified through mathematical decomposition of the raw images. The resulting decomposition magnitudes can then be used in conjunction with a variety of regression or classification algorithms to estimate either the pressure exerted by the finger or a qualitative measure such as "light touch" and "heavy touch". Such pressure estimates can be used, for example, to determine appropriate biometric templates to use for comparison with the acquired images, to determine whether the pressure is characteristic of the individual, to help detect certain types of spoof attempts, etc.

In another embodiment, the raw images can be processed and combined in a variety of ways to produce representations that emphasize the coarse and fine details of the fingerprint. For example, the collection of images similar to those in FIG. 3 can be transformed by taking the logarithm of the gray values. This set of log-images can then be filtered in a variety of ways to separate fingerprint features and other fine spatial details. For example, a set of smoothed log-images can be generated by convolving the log-images with a Gaussian kernel of some size. The smoothed images can then be subtracted from the original images to yield a set of images that emphasize fine details. These resulting images can then be averaged together according to the illumination wavelength (e.g., by averaging all images illuminated by red light separately from those acquired using green light and blue light). The resulting image can then be displayed as a single color image by concatenating the average red, green and blue images.

Figure 8:
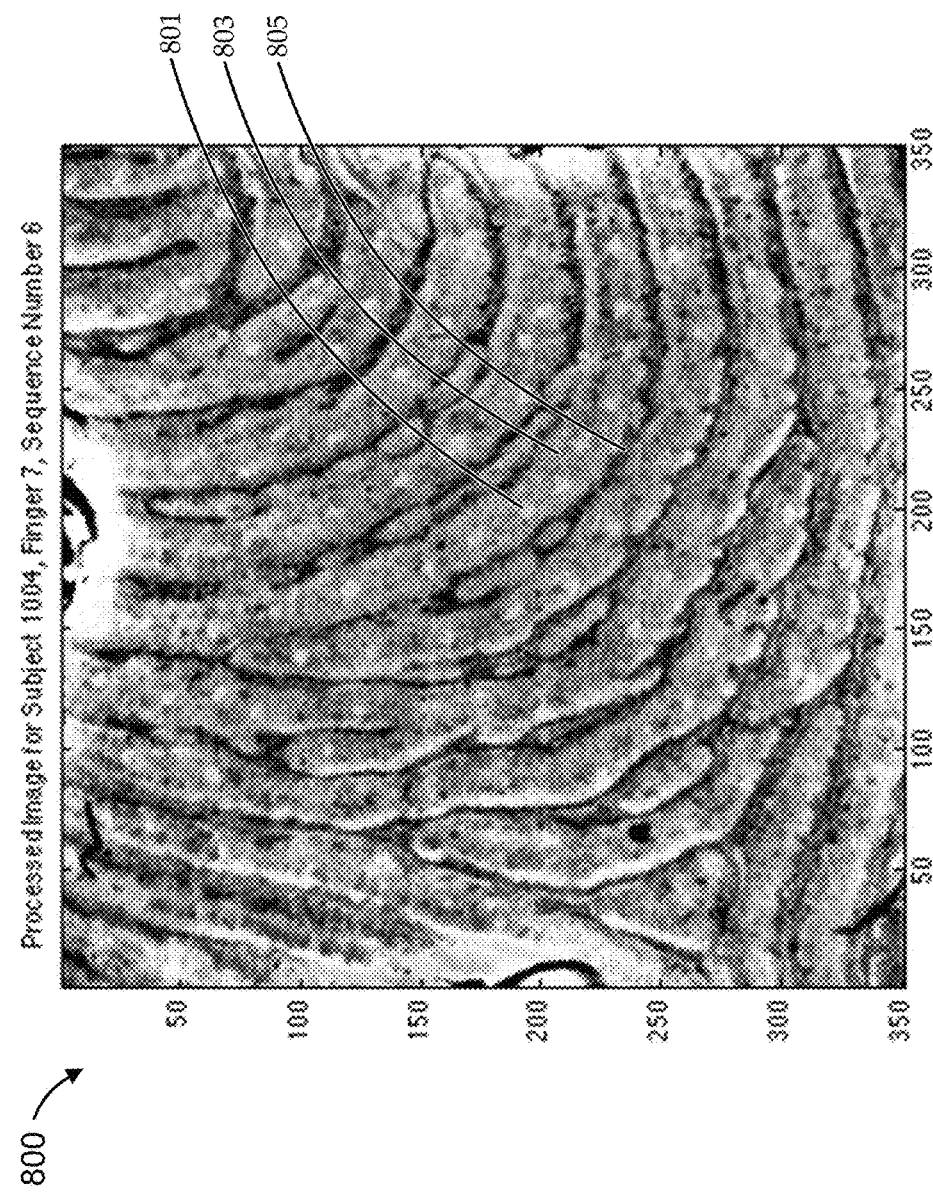
FIG. 8 shows an illustrative processed fingerprint image acquired with a biometric sensor, according to various embodiments (COLOR)

FIG. 8 shows an illustrative processed fingerprint image 800 acquired with a biometric sensor, according to various embodiments. The image 800 was generated using a technique similar to the one described above. However, there is a large number of different mathematical operations that may be performed in many different combinations and orders to achieve similar results. The raw images used to generate the image 800 of FIG. 8 can be represented in a variety of alternative ways, including by applying a decorrelation stretching algorithm across all (e.g., twelve) original images, or alternatively by combining all original images into a signal gray-scale image. While any such operations can be useful for certain functions, the RGB format of FIG. 8 can be particularly useful to demonstrate an observation made by the inventors regarding how pores and other structures of the fingerprint manifest themselves as a function of illumination wavelength. For example, there are a large number of pores visible in FIG. 8 (one of which is labeled as pore 801). As can be seen, these fine details are represented as a different color than the surrounding ridge 803 or valley 805 of the fingerprint. The valley 805 is relatively dark and gray, which can indicate that valleys are relatively dark features under all three illumination wavelengths used to generate the image 800. In contrast, the ridge 803 turns a red color, which can indicate that ridges become disproportionally light under red illumination relative to blue and green. Furthermore, the pore 801 is cyan, which can indicate that the pore 801 is relatively bright under blue and green illumination, but relatively dark under red illumination. Such differences suggest that it can be beneficial to analyze such differently illuminated images separately or in a way that maintains information, even when contrast of a feature changes polarity across illumination wavelengths or other conditions.

Figure 9:
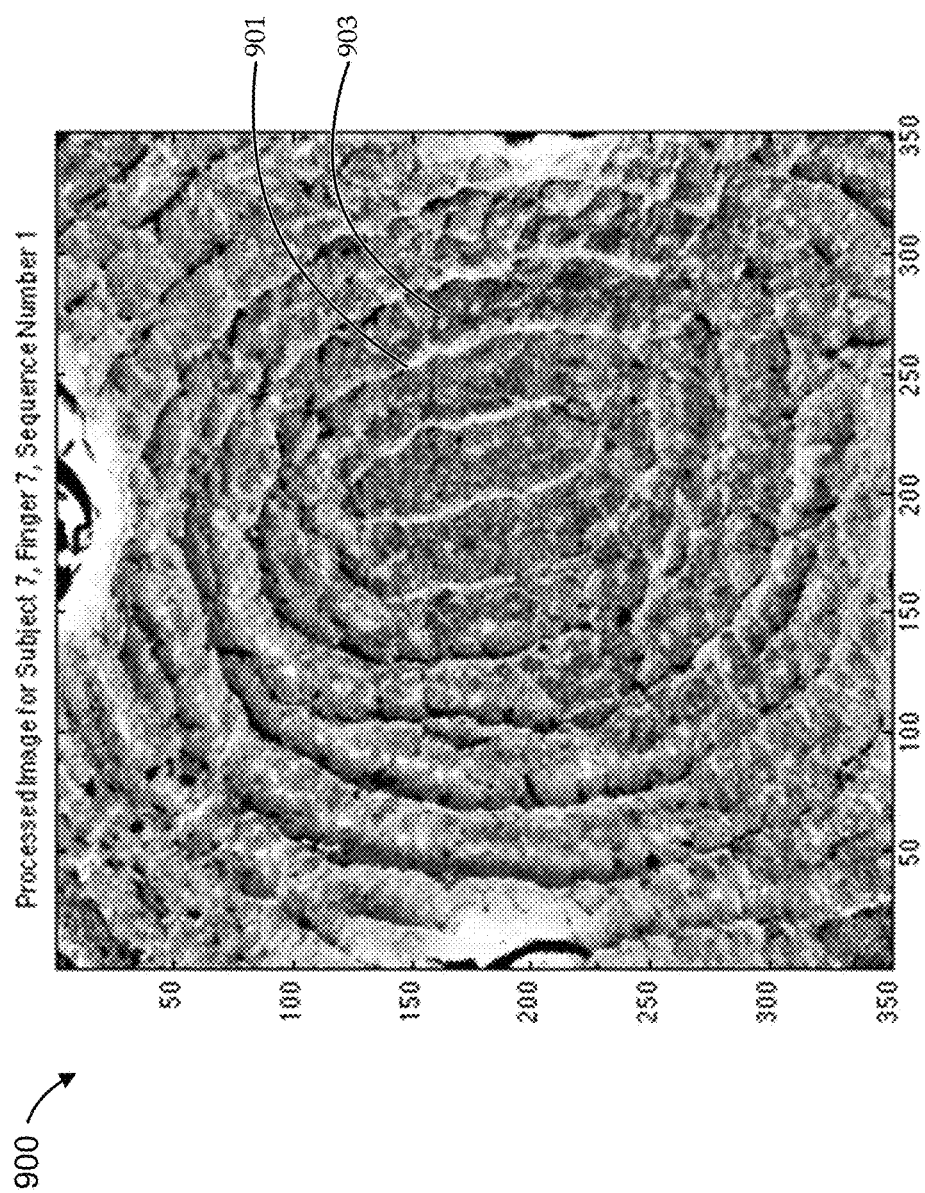
FIG. 9 shows an image, similar to the one shown in FIG. 8, acquired on a person with distinctly dry skin (COLOR)

FIG. 9 shows an image 900, similar to the one shown in FIG. 8, acquired on a person with distinctly dry skin. Although the pores are less pronounced than those in FIG. 8, it is evident that different features of the skin are manifested differently under the 3 illumination wavelengths. For example, as illustrated, the valleys 901 are a different color (blue) than the ridges 903 (*red*).

Figure 10:
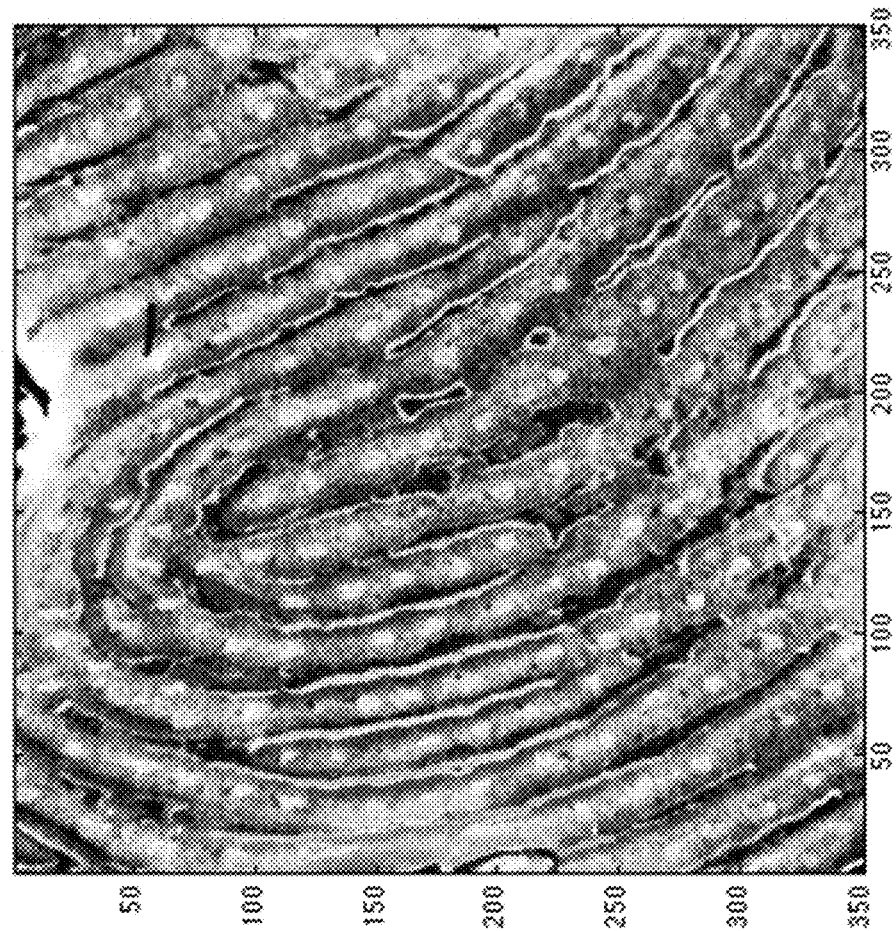
FIG. 10 shows an image, similar to the ones shown in FIGS. 8 and 9, acquired on a person with distinctly wet skin (COLOR)

FIG. 10 shows an image 1000, similar to the ones shown in FIGS. 8 and 9, acquired on a person with distinctly wet skin. Experimentally, this image was acquired after a subject's finger was dipped into a container of water and then immediately placed on a platen of a biometric sensor without first shaking, wiping, or otherwise removing water from the fingertip. As can be seen, the details of the fingerprint are well resolved under this extreme wet condition following the same procedure outlined above.

Figure 11:
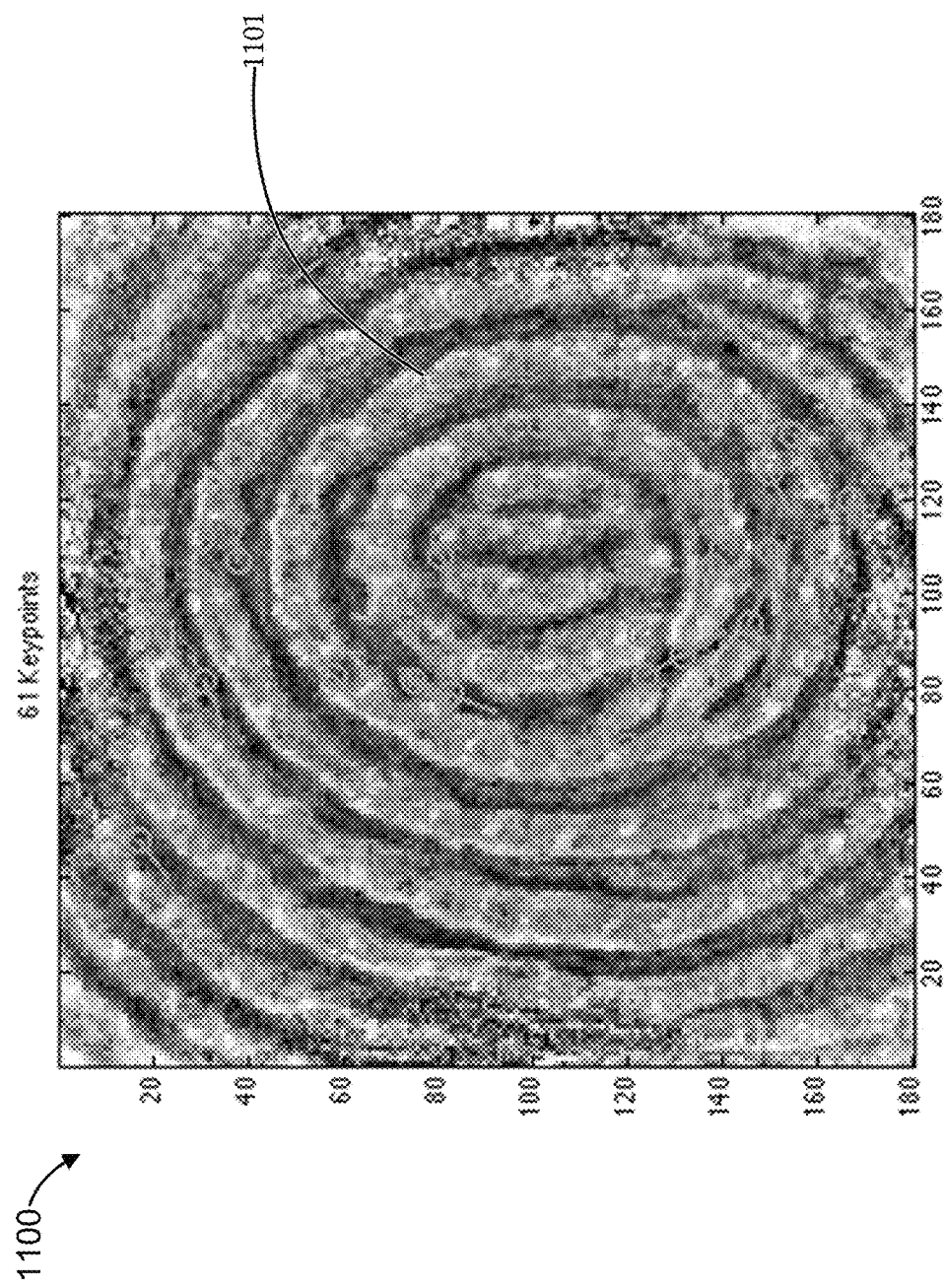
FIG. 11 shows a fingerprint image to which a keypoint detector has been applied (COLOR)

Some embodiments include one or more salient point detectors (e.g., "keypoint" detectors, "corner" detectors, etc.) to process raw data, or to further process otherwise processed data from acquired images. FIG. 11 shows a fingerprint image 1100 to which a keypoint detector has been applied. The circles show the detected keypoints 1101 and the lines show the orientation of the keypoints 1101. For example, each keypoint 1101 can be characterized by the dominant direction of local fingerprint characteristics. Each keypoint 1101 can be further characterized by a summary of the fingerprint characteristics proximal to the keypoint. Certain implementations can exploit large apparent inconsistencies between micro-level (e.g., pixel-level) flows and macro-level flows. For example, implementations can determine keypoints 1101 by computing a corner in a color gradient (e.g., using a Harris corner detector approach or other structure tensors approach, etc.).

In some embodiments, each keypoint 1101 can be matched to other keypoints 1101 that were generated from a plurality of images generated during a second measurement session to determine if the two fingers used in the two measurement sessions were likely to be the same finger. For example, first keypoints 1101 can be detected (computed) on a set of images acquired during enrollment of a subject, second keypoints 1101 can be detected on a set of images acquired during subsequent authentication of the subject, and the authentication can be based at least in part on comparing the first and second keypoints 1101.

Figure 12:
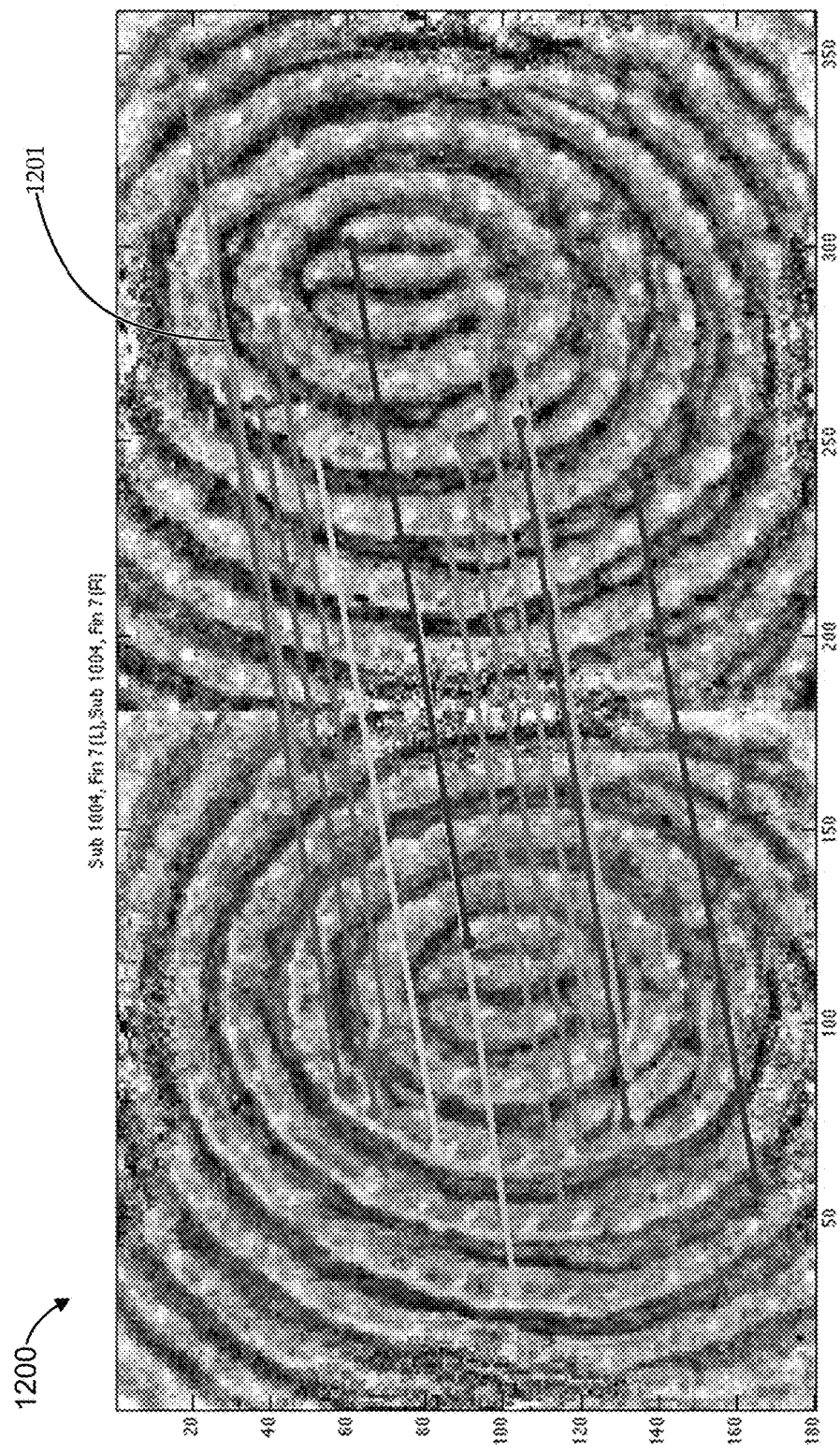
FIG. 12 illustrates shows an image comparison indicating matching sets of keypoints generated on different images acquired from the same finger (COLOR)

Images may be matched by comparing the keypoints 1101 in a variety of ways. For example, matching algorithms, such as SIFT (Scale-Invariant Feature Transform), SURF (Speeded Up Robust Feature), and/or other techniques, can be used to determine a match. FIG. 12 illustrates shows an image comparison 1200 indicating matching sets of keypoints 1201 generated on different images acquired from the same finger. Prior to matching the fingerprint pattern, the first image being matched can be generated by creating a mosaic (e.g., a tiling or composite) of individual images known to be from the same finger. Such a composite image can be generated during enrollment by an authorized user, for example, who would be prompted to touch the sensor multiple times. The resulting set of images can then be combined to form a composite image using a matching technique, such as those described above. The resulting composite enrollment image can spans a larger area than any one image, and therefore can be more tolerant of differences in finger placement during subsequent identification or verification of the user.

While in certain embodiments described above, the illumination subsystem and detection subsystem can both make contact with the skin, either or both subsystems may be configured such that no skin contact is necessary. For example, the illumination subsystem can include a light source and some means to focus the light to a point or other shape using a lens, lenses, mirrors, and/or other such means. This focused light can be incident on a region of skin that is different from the region being imaged. In particular, the focused illumination light can be incident near an edge of the region being imaged. Similarly, the imaging of the desired skin region can be accomplished without contact by using one or more lenses, mirrors, and/or other such means to image the skin on to the image array.

Figure 13:
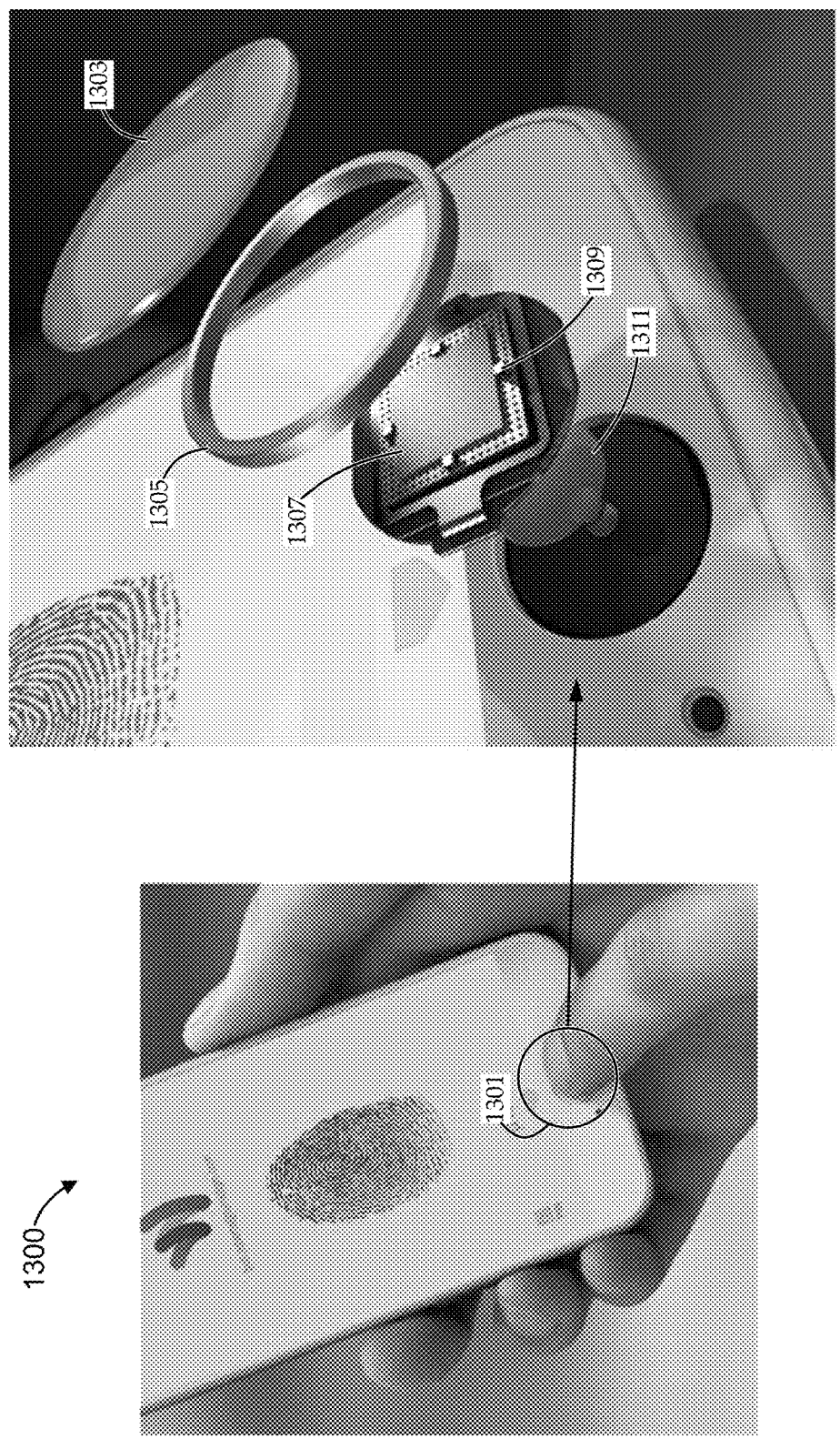
FIG. 13 shows an illustrative miniaturized biometric sensor integrated with a physical interface (e.g., a "home" button) of a portable electronic device (e.g., a smart phone) (COLOR)
Figure 14:
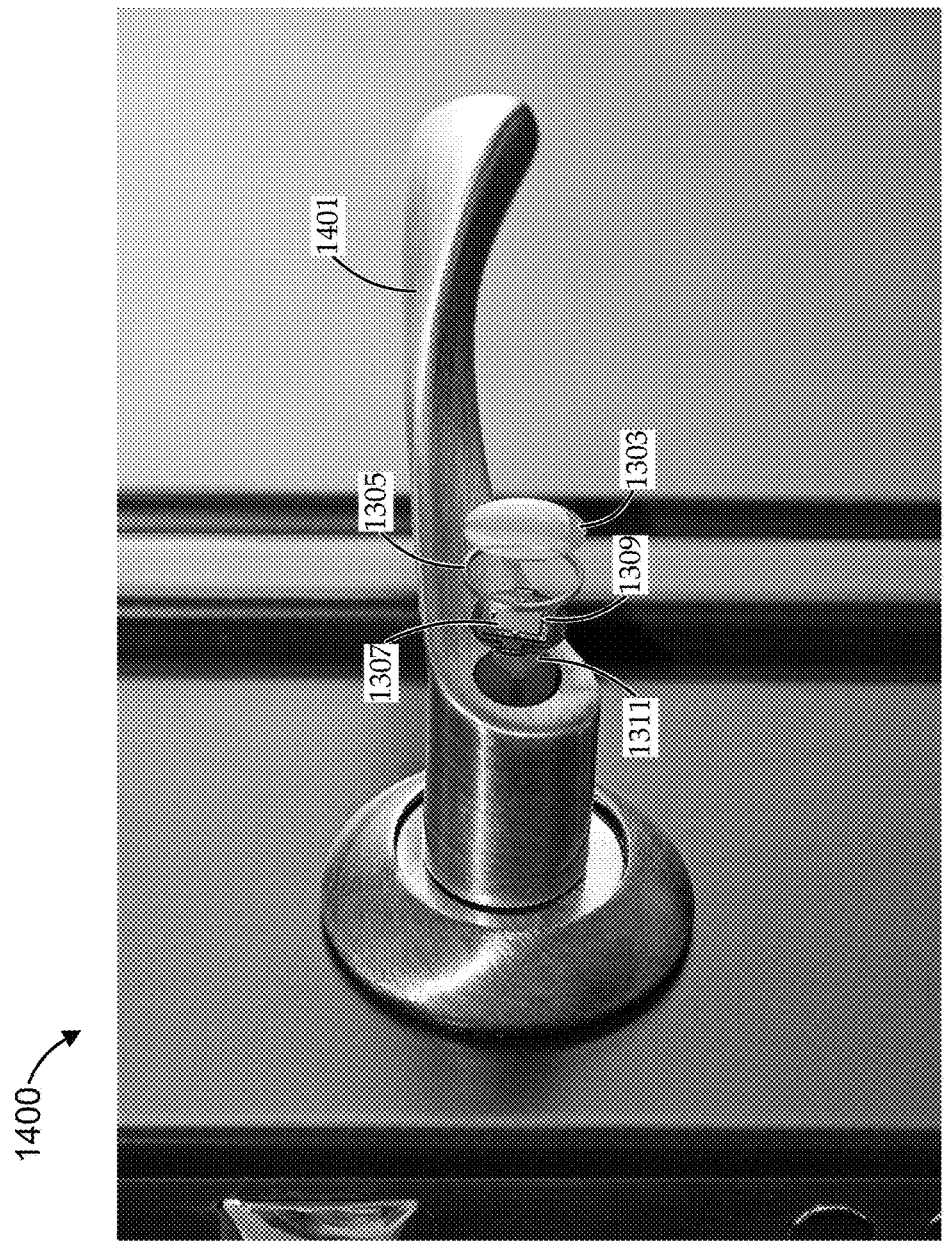
FIG. 14 shows an illustrative miniaturized biometric sensor integrated with a physical interface (e.g., a handle) of a mechanical locking mechanism (e.g., a door or drawer lock) (COLOR)

As described above, some embodiments can be implemented as miniaturized biometric sensors for integration into other mechanical and/or electronic systems. Some such integrations are illustrated in FIGS. 13 and 14. FIG. 13 shows an illustrative miniaturized biometric sensor integrated with a physical interface 1301 (e.g., a "home" button) of a portable electronic device (e.g., a smart phone). Alternatively, the sensor can be integrated with the portable electronic device in other ways, for example, as a separate feature from any other interface element. In one implementation, the sensor can be integrated into a mechanical button that can be pressed to make an electrical contact and also capable of acquiring and matching the user's biometric information. For example, pressing the button can activate the sensor, thereby causing one or more biometric images to be acquired via the sensor. The biometric sensor can then determine if the button was pressed by a genuine finger (as opposed to a spoof, other body part, etc.) and/or can perform one or more biometric functions, such as identifying the user, verifying an identity of the user, estimating the user's demographic characteristics (e.g., age, gender, ethnicity, profession, etc.), etc. In other implementations, presence of a finger can be detected without depressing the button, so that the sensor is only activated to capture an image after presence of the finger is detected (e.g., or when prompted, when requested, etc.). For example, presence detection can be based on capacitive sensing, resistive sensing, impedance sensing, mechanical sensing, and/or any other suitable techniques. Additionally or alternatively, presence detection can involve monitoring the imaging array to determine whether the array is receiving illumination, whether the spectral content is consistent with the output of sources, whether the detector output is consistent with receipt of illumination from skin of a person, etc.

FIG. 13 further shows an exploded view of the illustrative implementation of the miniaturized biometric sensor. As illustrated, the sensor includes a fiber optic faceplate 1303, an imaging array 1307, illumination sources 1309, and presence detection means 1305. The sensor is combined with a mechanical switch 1311. The imaging array 1307 can be a silicon array and can include a color filter array. The illumination sources 1309 can be LEDs and may be monochromatic of a variety of colors, white-light LEDs, triplets or other combinations of die, etc. The mechanical switch 1311 can be a membrane switch, a piezoelectric switch, and/or other suitable switch. In some implementations, information from the imaging array 1307 can be processed using on-board processing, processing resources of the portable electronic device, and/or external resources (e.g., accessed via wireless networking) to implement any of the biometric and/or other functionality described above. For example, biometric functionality facilitated by the sensor can provide secure access to the portable electronic device, and/or so can captures biometric information for use by a system other than the portable electronic device (e.g., a secured external system, such as an external computer system, automated teller machine (ATM), automobile or heavy machinery control, secured area, retail point-of-sale system, keyless entry device, etc.). Alternatively, embodiments can be combined with the general purpose camera functionality of a smart phone or other mobile device or as part of web camera functionality built into many computer monitors and other devices. The construction of such a device can include a variable-focus lens to focus on the finger for biometric sensing and/or to change focus for imaging distant external objects for general purpose imaging applications.

Many other access control applications can be implemented by integrating embodiments of the miniaturized biometric sensor described herein. FIG. 14 shows an illustrative miniaturized biometric sensor integrated with a physical interface 1401 (e.g., a handle) of a mechanical locking mechanism (e.g., a door or drawer lock). For example, the sensor can be dimensioned to fit into an opening for the barrel of a conventional key-based locking mechanism (e.g., generally having a diameter of no more than about ½ inch and a depth of no more than about 2 inches), and can be retrofit into existing hardware or custom designed into new hardware. In either case, the logic of the sensor system can drive conventional electromechanical elements to actuate locking/unlocking mechanisms. In the illustrated implementation, the mechanical locking assembly is moveable between locked and unlocked positions to enable and disable opening of a restricted access area. A handle 1401 is provided for opening the restricted access area when unlocked, and the biometric sensor is physically integrated with the handle and in communication with the mechanical locking assembly, so that the mechanical locking assembly is moveable to its unlocked position according to whether the subject is biometrically authorized by the biometric sensor. Similar physical access applications exist in many segments including automotive and/or industrial equipment (e.g., integrated into instrument controls, cab access, etc.); service and repair of sensitive systems; dangerous or otherwised controlled material handling; access to weapons systems (e.g., integrated into a trigger or safety mechanism, a storage cabinet, etc.), etc.

Figure 15:
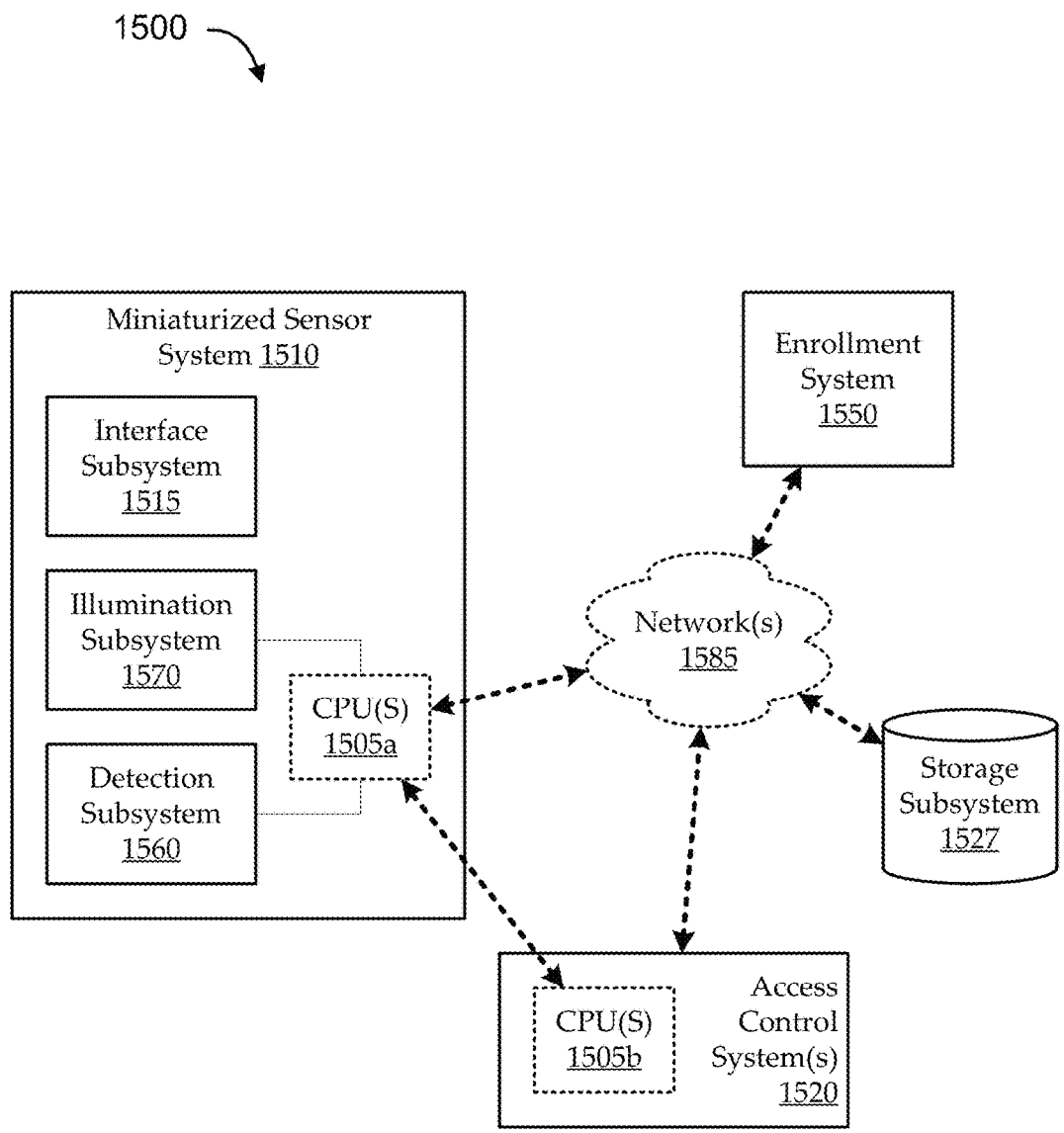
FIG. 15 shows a block diagram of an illustrative biometric scanning environment having various interconnected systems, according to various embodiments.

FIG. 15 shows a block diagram of an illustrative biometric scanning environment 1500 having various interconnected systems, according to various embodiments. The environment 1500 includes a miniaturized sensor system 1510, which can be implemented as as described herein. For example, the miniaturized sensor system 1510 includes an interface subsystem 1515, an illumination subsystem 1570, and a detection subsystem 1560. In some implementations, functionality of the illumination subsystem 1570 and/or the detection subsystem 1560 can be controlled, at least in part, by a set of (i.e., one or more) processors 1505. The processors 1505 can include dedicated controllers (e.g., an illumination controlled, LED driver, imaging controller, graphics processor, etc.), general purpose central processing units (CPUs), or any other suitable type of processor 1505. Further, as illustrated, the processors 1505 can be integrated with the miniaturized sensor system 1510 and/or "off-board" (e.g., the miniaturized sensor system 1510 can use processing functionality of interconnected systems).

As illustrated, embodiments of the miniaturized sensor system 1510 can be in communication with one or more enrollment systems 1550, access control systems 1520, storage systems 1527, etc. Such communication can be through direct integration (e.g., the miniaturized sensor system 1510 can be integrated into an access control system 1520, such as an electromechanical lock), through direct connection (e.g., via a dedicated wired or wireless connection), through one or more networks 1585 (e.g., wired or wireless, local or remote, secured or unsecured, etc.), and/or in any other suitable manner.

In some embodiments, an individual enrolls a fingerprint using the miniaturized sensor system 1510. For example, during an enrollment routine, implementations capture multiple samples (e.g., ten or more) of an enrollee's fingerprint. Some implementations include a user interface or means to communicate with a user interface to prompt the enrollee to provide the multiple samples (e.g., by prompting to place the finger on the sensor multiple times, each time acquiring a sample and indicating whether the sample was acceptably acquired). The multiple samples can be used as individual templates for comparison against future authentication attempts and/or combined to form larger-area templates for future comparison. For example, the enrollment data can be stored in the storage system 1527 (e.g., using on-board storage of the miniaturized sensor system 1510, networked storage, storage resources of another interconnected system, etc.). When the individual later attempts to gain access using the miniaturized sensor system 1510, the miniaturized sensor system 1510 can acquire new biometric data, and compare the new biometric data with the stored biometric enrollment data to determine whether to authenticate the individual.

In other embodiments, an individual enrolls a fingerprint on a separate enrollment system 1550. Some enrollment systems 1550 can include a larger-area scanner, such as a conventional optical fingerprint reader (e.g., using TIR techniques, multispectral techniques, etc.), larger area sensors (e.g., configured to scan multiple fingerprints, palm prints, etc.), and/or other types of biometric scanners (e.g., iris scanners, voice recorders, etc.). For example, the miniaturized sensor system 1510 can be sized to image only a small portion of a fingerprint; so that reliable future matching can be facilitated by comparing the imaged small portion with a previously imaged larger portion of the fingerprint. This can be accomplished with the miniaturized sensor system 1510 alone by capturing a number of images of the fingerprint during enrollment (e.g., and stitching them together to form a larger imaged region, or using the images in conjunction for comparison). However, a larger-area scanner can form an image of a larger region of the fingerprint by acquiring a smaller number of sample images (e.g., one). For example, this can speed up the enrollment process and/or increase its reliability.

Notably, the images and/or processed data acquired during enrollment can be used as templates for comparison against future authentication attempts with one or more miniaturized sensor system 1510. Further, such biometric templates can be stored in a centralized storage system 1527 (i.e., one accessible by one or more instances of the miniaturized sensor system 1510. For example, a large facility may include a single enrollment system 1550 (e.g., a larger-area scanner in a security office) in communication with a highly secured storage system 1527 that maintains biometric templates and/or other data (e.g., demographics, access permissions, and/or other data about individuals that may be stored in association with their enrolled biometric data). The large facility can also include many access-controlled assets (e.g., rooms, storage cabinets, computer systems, etc.), each protected by a networked instance of the miniaturized sensor system 1510. When an individual attempts to access one of the access-controlled assets using the respective miniaturized sensor system 1510 instance, acquired biometrics can be compared against the securely stored enrollment data to determine and affect access privileges.

Similar functionality can be provided if an instance of the miniaturized sensor system 1510 is used for enrollment. For example, an individual can enroll his fingerprint using a miniaturized sensor system 1510 instance integrated into a portable electronic device. When the individual attempts to access an asset controlled by a second instance of the miniaturized sensor system 1510, the second instance can acquire new biometric data from the individual, communicate with the portable electronic device (or other off-board storage), and compare the enrollment data to determine and affect access.

Figure 16:
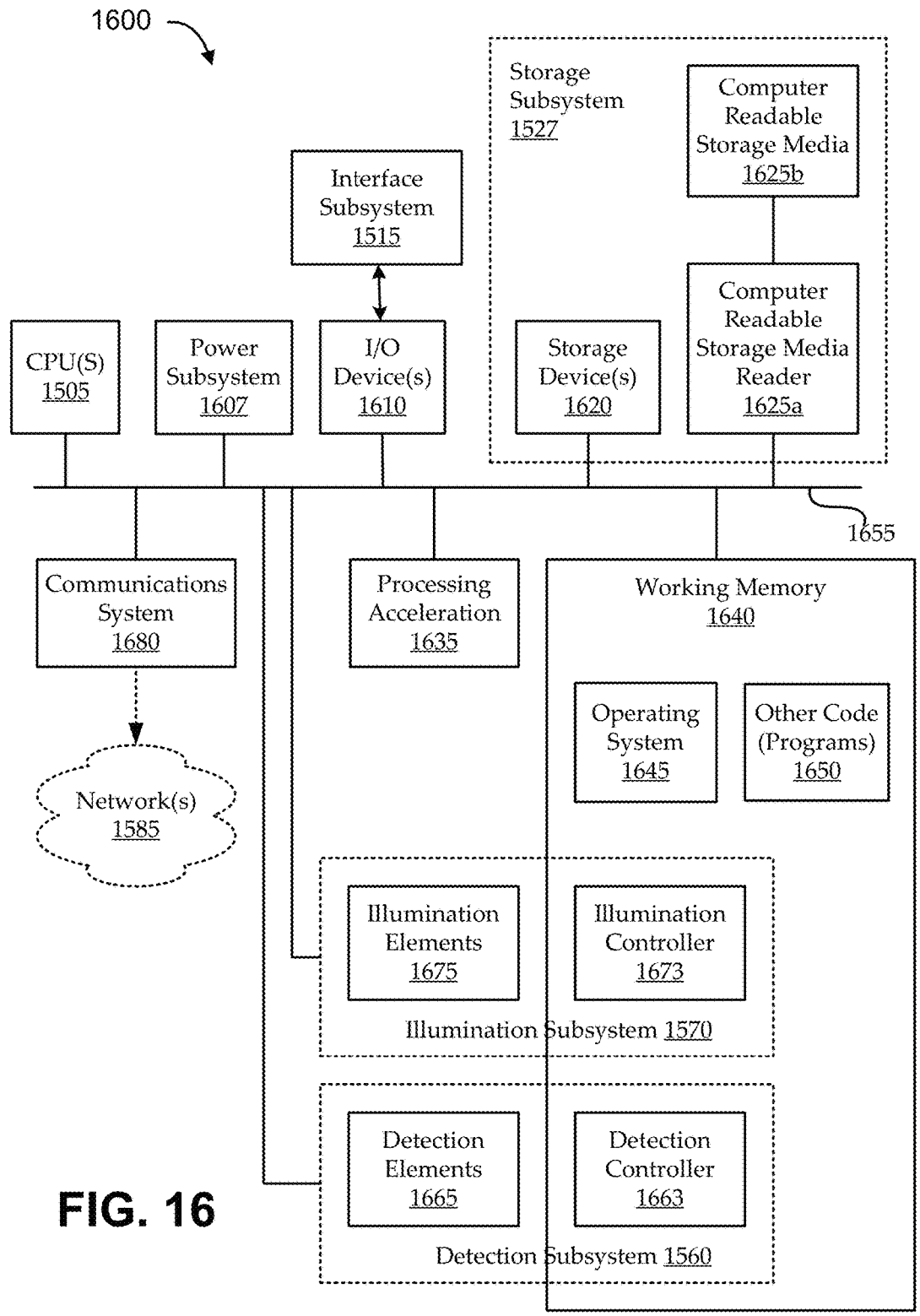
FIG. 16 shows an exemplary computational environment for implementing a biometric sensor system, according to various embodiments.

Various functionality described above can be implemented in one or more computational environments. FIG. 16 shows an exemplary computational environment 1600 for implementing a biometric sensor system, according to various embodiments. The computational environment 1600 can be implemented as or embodied in single or distributed computer systems, or in any other useful way. The computational environment 1600 is shown including hardware elements that may be electrically coupled via a bus 1655.

The hardware elements may include one or more central processing units (CPUs) and/or other processor(s) 1505 (e.g., as described with reference to FIG. 15). Implementations can also include one or more input/output devices 1610, which can include and or be integrated with an interface subsystem 1515, as described above. Some implementations also include a power subsystem 1607, including any suitable power storage, power electronics, power interfaces, etc. Some implementations can permit data to be exchanged, via a communications subsystem 1680, with one or more networks 1585 and/or any other computer or external system (e.g., as described above with respect to FIG. 15). The communications subsystem 1680 can include a modem, a network card (wireless or wired), an infrared communication device, and/or any other suitable components or combinations thereof.

The computational environment 1600 can also include one or more storage devices 1620. By way of example, storage device(s) 1620 may be disk drives, optical storage devices, solid-state storage device such as a random access memory (RAM) and/or a read-only memory (ROM), which can be programmable, flash-updateable and/or the like. The computational environment 1600 can additionally include a computer-readable storage media reader 1625a, and working memory 1640, which may include RAM and ROM devices as described above. The computer-readable storage media reader 1625a can further be connected to a computer-readable storage medium 1625b, together (and, optionally, in combination with storage device(s) 1620) comprehensively representing remote, local, fixed, and/or removable storage devices plus storage media for temporarily and/or more permanently containing computer-readable information. The storage device(s) 1620, computer-readable storage media and media reader 1625, and/or working memory 1640 can be implemented as a storage subsystem 1527 (e.g., as illustrated in FIG. 15). In some embodiments, the computational environment 1600 can also include a processing acceleration unit 1635, which can include a DSP, a special-purpose processor and/or the like.

The computational environment 1600 may also include software elements, shown as being currently located within a working memory 1640, including an operating system 1645 and/or other code 1650, such as an application program (which may be a client application, web browser, mid-tier application, etc.). For example, embodiments can be implemented as instructions, which, when executed by one or more processors 1505, cause the processors 1505 to perform certain functions. Such functions can include functionality of an illumination controller 1673 (which can direct operation of illumination elements 1675 as part of an illumination subsystem 1570) and a detection controller 1663 (which can direct operation of detection elements 1665 as part of a detection subsystem 1560), for example, as described above.

A software module can be a single instruction, or many instructions, and can be distributed over several different code segments, among different programs, and across multiple storage media. Thus, a computer program product may perform operations presented herein. For example, such a computer program product may be a computer readable tangible medium having instructions tangibly stored (and/or encoded) thereon, the instructions being executable by one or more processors to perform the operations described herein. The computer program product may include packaging material. Software or instructions may also be transmitted over a transmission medium. For example, software may be transmitted from a website, server, or other remote source using a transmission medium such as a coaxial cable, fiber optic cable, twisted pair, digital subscriber line (DSL), or wireless technology such as infrared, radio, or microwave.

Alternate embodiments of a computational environment 1600 may have numerous variations from that described above. For example, customized hardware might also be used and/or particular elements might be implemented in hardware, software (including portable software, such as applets), or both. Further, connection to other computing devices such as network input/output devices may be employed. Software of the computational environment 1600 may include code 1650 for implementing embodiments of the present invention as described herein. For example, while not shown as part of the working memory 1640, certain functionality of other subsystems (e.g., the interface subsystem 1515, storage subsystem 1527, etc.) can be implemented with any suitable combination of hardware and software, including using code 1650 stored in the working memory 1640.

Figure 17:
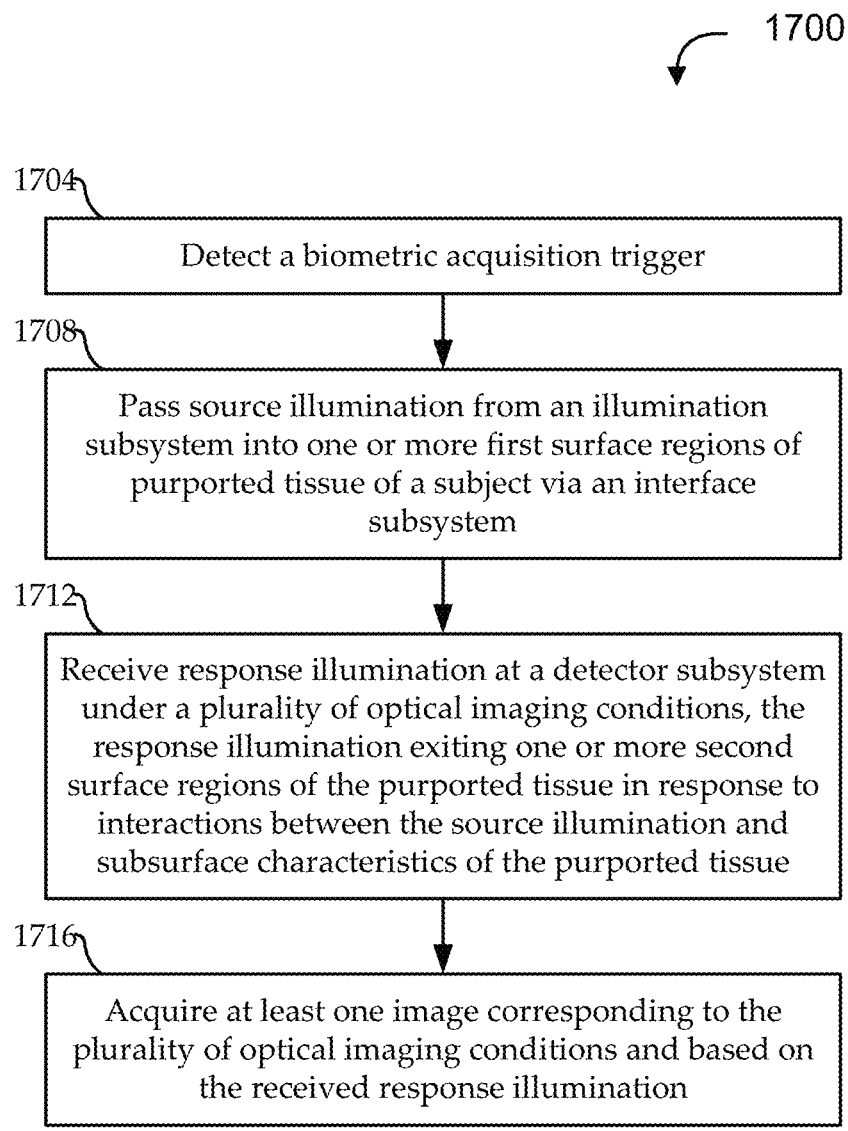
FIG. 17 shows a flow diagram of an illustrative method for providing access control using embodiments of biometric sensors described herein.

FIG. 17 shows a flow diagram of an illustrative method 1700 for providing access control using embodiments of biometric sensors described herein. Embodiments begin at stage 1704 by detecting a biometric acquisition trigger. The biometric acquisition trigger can include presence detection, interaction with an electromechanical interface integrated with the sensor, prompting, etc. At stage 1708, source illumination can be passed from an illumination subsystem (e.g., one or more illumination sources that may or may not be coupled with optical guides, or the like) into one or more first surface regions of purported tissue of a subject via an interface subsystem (e.g., a platen, fiber-optic face plate, etc.). Response illumination can be received at a detector subsystem under a plurality of optical imaging conditions at stage 1712. The response illumination can be the illumination exiting one or more second surface regions of the purported tissue (i.e., different from the first surface regions) in response to interactions between the source illumination and subsurface characteristics of the purported tissue. For example, implementations can be configured so that source illumination cannot be received by the detection subsystem until it first passes through the subsurface of the purported tissue, thereby becoming response illumination. At stage 1716, at least one image can be acquired corresponding to the plurality of optical imaging conditions and based on the received response illumination. In various embodiments, the acquired image can be processed to perform one or more functions, such as identifying a user, verifying identity of a user, estimating demographic characteristics of a user, affecting access to secure assets (e.g., secure locations, devices, materials, etc.), etc.

The methods disclosed herein include one or more actions for achieving the described method. The method and/or actions may be interchanged with one another without departing from the scope of the claims. In other words, unless a specific order of actions is specified, the order and/or use of specific actions may be modified without departing from the scope of the claims.

Other examples and implementations are within the scope and spirit of the disclosure and appended claims. For example, features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

Various changes, substitutions, and alterations to the techniques described herein can be made without departing from the technology of the teachings as defined by the appended claims. Moreover, the scope of the disclosure and claims is not limited to the particular aspects of the process, machine, manufacture, composition of matter, means, methods, and actions described above. Processes, machines, manufacture, compositions of matter, means, methods, or actions, presently existing or later to be developed, that perform substantially the same function or achieve substantially the same result as the corresponding aspects described herein may be utilized. Accordingly, the appended claims include within their scope such processes, machines, manufacture, compositions of matter, means, methods, or actions.

What is claimed is:

1. A biometric access system comprising:
a biometric sensor comprising:
an interface subsystem comprising an interface surface disposed to contact purported tissue of a subject;
an illumination subsystem disposed to pass source illumination into the purported tissue of a subject via a set of first surface regions of the purported tissue;
a detector subsystem disposed to acquire an image stack comprising a plurality of images, each image acquired from response illumination exiting a set of second surface regions of the purported tissue, the set of second surface regions being different from the set of first surface regions, the response illumination produced by interactions between the source illumination and subsurface characteristics of the purported tissue,
such that the plurality of images comprises a first set of images acquired under a first optical imaging condition at each of a plurality of exposure times, and a second set of images acquired under a second optical imaging condition at each of the plurality of exposure times; and
a processor disposed to generate combined image data from a combination of the first and second sets of images, and to output a biometric determination relating to the purported tissue as a function of the combined image data.

2. The biometric access system of claim 1, wherein the interface subsystem further comprises:
a shield disposed to substantially block the source illumination from reaching the detector subsystem without first entering the purported tissue.

3. The biometric access system of claim 1, wherein the interface subsystem further comprises:
a set of optical guides disposed to guide the source illumination from the illumination subsystem to the set of first surface regions, thereby substantially blocking the source illumination from reaching the detector subsystem without first entering the purported tissue.

4. The biometric access system of claim 3, wherein the set of optical guides are instantiated in a fiber-optic faceplate, and the interface surface is integrated with the fiber-optic faceplate.

5. The biometric access system of claim 1, wherein the detector subsystem is further disposed to detect presence of the purported skin site with respect to the interface surface prior to acquiring the plurality of images.

6. The biometric access system of claim 1, wherein a wavelength of the source illumination is different between each of the first optical imaging condition and the second optical imaging condition.

7. The biometric access system of claim 1, wherein:
the set of first surface regions comprises a plurality of first surface regions;
the illumination subsystem comprises a plurality of illumination sources; and
each illumination source is disposed to pass a respective portion of the source illumination into the purported tissue via a respective one of the first surface regions.

8. The biometric access system of claim 7, wherein the each illumination source is disposed to provide a different wavelength of illumination.

9. The biometric access system of claim 1, wherein the detector system further comprises a set of optics, and each of the first optical imaging condition and the second optical imaging condition is affected by the response illumination and the set of optics.

10. The biometric access system of claim 1, wherein the detector subsystem comprises an imaging array disposed to generate the plurality of images, the imaging array having an array of pixels that provides information that is spatially correlated to imaged regions of the purported tissue.

11. The biometric access system of claim 10, wherein
the biometric determination comprises differentiating between the purported tissue being genuine tissue and a spoof according to a spatiospectral analysis of the combined image data.

12. The biometric access system of claim 1, wherein
the biometric determination comprises biometrically authorizing the subject by processing the combined image data.

13. The biometric access system of claim 12, wherein biometrically authorizing the subject comprises:
computing a first plurality of keypoints in the plurality of images; and
comparing the first plurality of keypoints with a second plurality of keypoints associated with previously stored biometric information.

14. The biometric access system of claim 13, wherein:
the plurality of images comprises multispectral information; and
each of the first plurality of keypoints is computed as a corner in a spatial gradient of at least one of the plurality of images.

15. The biometric access system of claim 1, wherein the processor is disposed to output the biometric determination by identifying the subject or verifying the identity of the subject as a function of the combined image data.

16. The biometric access system of claim 1, wherein the processor is disposed to output the biometric determination according to a biometric template corresponding to the subject and generated during prior biometric enrollment of the subject.

17. The biometric access system of claim 16, wherein the biometric sensor is a miniaturized biometric sensor, and the prior biometric enrollment of the subject was performed on a non-miniaturized biometric sensor.

18. The biometric access system of claim 1, further comprising:
a physical interface of a portable communications device, the physical interface having the biometric sensor integrated therewith, and the physical interface disposed to permit access by the subject to the portable communications device when the subject is biometrically authorized by the biometric sensor,
wherein the subject is biometrically authorized in response to detecting that the output of the biometric determination indicates that the subject is biometrically authorized.

19. The biometric access system of claim 1, further comprising:
a mechanical locking assembly moveable between locked and unlocked positions to enable and disable opening of a restricted access area; and
a handle for opening the restricted access area when unlocked,
wherein the biometric sensor is physically integrated with the handle and in communication with the mechanical locking assembly, so that the mechanical locking assembly is moveable to its unlocked position according to whether the subject is biometrically authorized by the biometric sensor, and wherein the subject is biometrically authorized in response to detecting that the output of the biometric determination indicates that the subject is biometrically authorized.

20. The biometric access system of claim 1, wherein:
the processor is disposed to generate the combined image data from the combination of the first and second sets of images by compositing the plurality of images into a single, color image of the set of second surface regions.

* * * * *